(12) United States Patent
Doles

(10) Patent No.: US 12,318,314 B2
(45) Date of Patent: *Jun. 3, 2025

(54) SYSTEM AND METHODS FOR RESIDUAL LIMBS OF AMPUTEES

(71) Applicant: JSG IP Ventures, LLC, Greenwood Village, CO (US)

(72) Inventor: Jordan T. Doles, Fort Collins, CO (US)

(73) Assignee: JSG IP Ventures, LLC, Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/667,137

(22) Filed: May 17, 2024

(65) Prior Publication Data
US 2024/0299191 A1  Sep. 12, 2024

Related U.S. Application Data

(60) Continuation of application No. 18/510,337, filed on Nov. 15, 2023, now Pat. No. 11,986,402, which is a
(Continued)

(51) Int. Cl.
*A61F 2/72* (2006.01)
*A61B 5/00* (2006.01)
(Continued)

(52) U.S. Cl.
CPC ............... *A61F 2/50* (2013.01); *A61B 5/377* (2021.01); *A61B 5/6811* (2013.01); *A61F 2/72* (2013.01);
(Continued)

(58) Field of Classification Search
CPC ...... A61F 2/50; A61F 2/72; A61F 2/68; A61F 2/70; A61F 2/7812; A61F 2002/608;
(Continued)

(56) References Cited

U.S. PATENT DOCUMENTS

| 4,142,532 A | 3/1979 | Ware |
| 5,044,368 A | 9/1991 | Putz |

(Continued)

FOREIGN PATENT DOCUMENTS

| DE | 102015009828 A1 | 2/2017 |
| DE | 102021125702 A1 | 4/2022 |

(Continued)

OTHER PUBLICATIONS

System for Excitation of Phantom Sensations, Meier-Koll et al., translation for DE 102015009828 (Year: 2017).*

(Continued)

*Primary Examiner* — Bruce E Snow
(74) *Attorney, Agent, or Firm* — Holland & Hart LLP

(57) ABSTRACT

Various aspects of this disclosure relate to a prosthetic cover comprising an array of sensors, which transmit signals to an array of electrodes in a liner that fits over a residual limb of an amputee. Different interactions with the prosthetic cover cause different activation of the electrodes to transmit electrical current through different areas of the residual limb and modulate neurons differently within the residual limb.

25 Claims, 10 Drawing Sheets

Related U.S. Application Data division of application No. 18/296,970, filed on Apr. 6, 2023, now Pat. No. 11,833,064.

(60) Provisional application No. 63/348,967, filed on Jun. 3, 2022.

(51) Int. Cl.
| | | |
|---|---|---|
| *A61B 5/377* | (2021.01) | |
| *A61F 2/50* | (2006.01) | |
| *A61F 2/70* | (2006.01) | |
| *A61F 2/78* | (2006.01) | |
| *A61N 1/36* | (2006.01) | |
| *A61F 2/60* | (2006.01) | |
| *A61F 2/68* | (2006.01) | |

(52) U.S. Cl.
CPC ...... *A61N 1/3606* (2013.01); *A61F 2002/608* (2013.01); *A61F 2/68* (2013.01); *A61F 2002/6827* (2013.01); *A61F 2/70* (2013.01); *A61F 2/7812* (2013.01)

(58) Field of Classification Search
CPC ............. A61F 2002/6827; A61B 5/377; A61B 5/6811; A61N 1/3606
See application file for complete search history.

(56) References Cited

U.S. PATENT DOCUMENTS

| | | | |
|---|---|---|---|
| 5,466,244 | A | 11/1995 | Morgan |
| 5,505,201 | A | 4/1996 | Grill et al. |
| 5,888,213 | A | 3/1999 | Sears et al. |
| 7,003,348 | B1 | 2/2006 | Brewer et al. |
| 7,107,097 | B2 | 9/2006 | Stern et al. |
| 7,697,995 | B2 | 4/2010 | Cross et al. |
| 8,945,236 | B2 | 2/2015 | Leiniger et al. |
| 9,358,138 | B2 | 6/2016 | Kelley et al. |
| 9,615,944 | B2 * | 4/2017 | Will ........................ A61F 2/76 |
| 10,617,354 | B2 | 4/2020 | Berg et al. |
| 11,577,045 | B2 | 2/2023 | Perry et al. |
| 11,809,629 | B1 | 11/2023 | Segil |
| 11,833,064 | B1 * | 12/2023 | Doles ....................... A61F 2/72 |
| 11,986,402 | B2 * | 5/2024 | Doles ................... A61N 1/3606 |
| 12,201,536 | B2 | 1/2025 | Doles et al. |
| 2006/0206162 | A1 | 9/2006 | Wahlstrand et al. |
| 2008/0312580 | A1 | 12/2008 | Barsness et al. |
| 2009/0216339 | A1 | 8/2009 | Hanson et al. |
| 2010/0298895 | A1 | 11/2010 | Ghaffari et al. |
| 2011/0118853 | A1 | 5/2011 | Kirn |
| 2012/0101595 | A1 | 4/2012 | Jung et al. |
| 2012/0296445 | A1 | 11/2012 | Leiniger et al. |
| 2013/0041235 | A1 | 2/2013 | Rogers et al. |
| 2014/0163444 | A1 | 6/2014 | Ingvarsson et al. |
| 2014/0188251 | A1 | 7/2014 | Mosler et al. |
| 2014/0277583 | A1 | 9/2014 | Kuntaegowdanahalli et al. |
| 2015/0142129 | A1 | 5/2015 | Kirn |
| 2015/0360030 | A1 | 12/2015 | Cartledge et al. |
| 2016/0015280 | A1 | 1/2016 | Hyde et al. |
| 2016/0263345 | A1 | 9/2016 | Shuster et al. |
| 2016/0331561 | A1 | 11/2016 | Raspopovic et al. |
| 2016/0346164 | A1 | 12/2016 | Ward et al. |
| 2017/0056682 | A1 | 3/2017 | Kumar et al. |
| 2017/0136238 | A1 | 5/2017 | Hartig et al. |
| 2017/0311827 | A1 | 11/2017 | Choi et al. |
| 2017/0348117 | A1 | 12/2017 | Strbac et al. |
| 2018/0153430 | A1 | 6/2018 | Ang et al. |
| 2018/0296822 | A1 | 10/2018 | Schroeder et al. |
| 2019/0254845 | A1 | 8/2019 | Wernke et al. |
| 2020/0139138 | A1 | 5/2020 | Sit et al. |
| 2020/0376272 | A1 | 12/2020 | Block et al. |
| 2021/0186719 | A1 | 6/2021 | Laghi et al. |
| 2022/0031480 | A1 | 2/2022 | Bause et al. |
| 2022/0386935 | A1 | 12/2022 | Lo et al. |
| 2023/0293318 | A1 * | 9/2023 | Kaltenborn ............... A61F 2/66 623/55 |
| 2023/0398004 | A1 | 12/2023 | Messner et al. |

FOREIGN PATENT DOCUMENTS

| | | |
|---|---|---|
| EP | 2962726 B1 | 11/2020 |
| WO | 2019/025838 A1 | 2/2019 |

OTHER PUBLICATIONS

"International Search Report and Written Opinion of the International Searching Authority," issued in connection with Int'l Appl. No. PCT/US2024/023642, dated Jul. 18, 2024 (14 pages).

Culp, C. J., "Current Understanding of Phantom Pain and its Treatment", Pain Physician, 2022, vol. 25, pp. E941-E957.

Mulvey et: "Transcutaneous Electrical Nerve Stimulation for Phantom Pain and Stump Pain in Adult Amputees", pp. 1-8. (Year: 2012).

* cited by examiner

SYSTEM AND METHODS FOR RESIDUAL LIMBS OF AMPUTEES

CROSS-REFERENCE TO RELATED APPLICATIONS

This patent application is a Continuation of U.S. patent application Ser. No. 18/510,337, filed Nov. 15, 2023, which is a Division of U.S. patent application Ser. No. 18/296,970, filed Apr. 6, 2023, which claims priority to U.S. Provisional Patent Application No. 63/348,967, filed Jun. 3, 2022, both of which are incorporated by reference in their entirety.

BACKGROUND

Amputees frequently suffer from phantom limb syndrome, in which they experience sensations that they attribute to a missing limb. These sensations are generally undesirable, frequently painful, and, in some cases, debilitating.

Phantom limb syndrome may be treated by mirror therapy, in which a mirror provides a visual representation of a missing limb when placed between intact and missing limbs. As patients move their intact limbs, two limbs appear to move concurrently. This provides patients with a visual representation of their missing limbs, which affects the way they feel their missing limbs following repeated therapy. Clinical research on mirror therapy has not, however, demonstrated a statistically significant effect on reducing pain.

Other non-pharmacological interventions to reduce symptoms of phantom limb syndrome remain desirable.

SUMMARY

Various aspects of this disclosure relate to the finding that neural feedback from interactions with a prosthesis can help alleviate symptoms of phantom limb syndrome. Some embodiments relate to a prosthetic cover comprising an array of sensors, which transmit signals to an array of electrodes in a liner that fits over a residual limb of an amputee. Different interactions with the prosthetic cover cause different activation of the electrodes to transmit electrical current through different areas of the residual limb and modulate neurons differently within the residual limb. An amputee can therefore interact with a prosthetic by touching the cover, viewing the interaction, and modulating different neurons in response to touch. Without limiting this specification or any patent claim that matures from this disclosure, simultaneous sensory feedback from touch, vision, and electrical current favorably induces neuroplasticity in the somatosensory cortex of the brain of an amputee to create a new topographic map for the prosthetic through repeated interaction, which reduces symptoms of phantom limb syndrome. Without limiting this specification or any patent claim that matures from this disclosure, the new topographic map allows amputees to associate specific symptoms of phantom limb syndrome with specific interactions with the prosthetic cover, which allows amputees to treat the specific symptoms as they arise via the specific interactions.

Various other aspects of the inventions of this disclosure will become apparent upon review of the following detailed description and claims. The scope of this disclosure shall not be limited by the foregoing summary and background. The scope of each patent claim that matures from this disclosure shall not be limited by the foregoing summary and background or by the following detailed description, and the scope of each patent claim that matures from this disclosure shall instead be limited solely by the explicit language of the claim in the context of its claim dependency.

DETAILED DESCRIPTION

Figure 1:
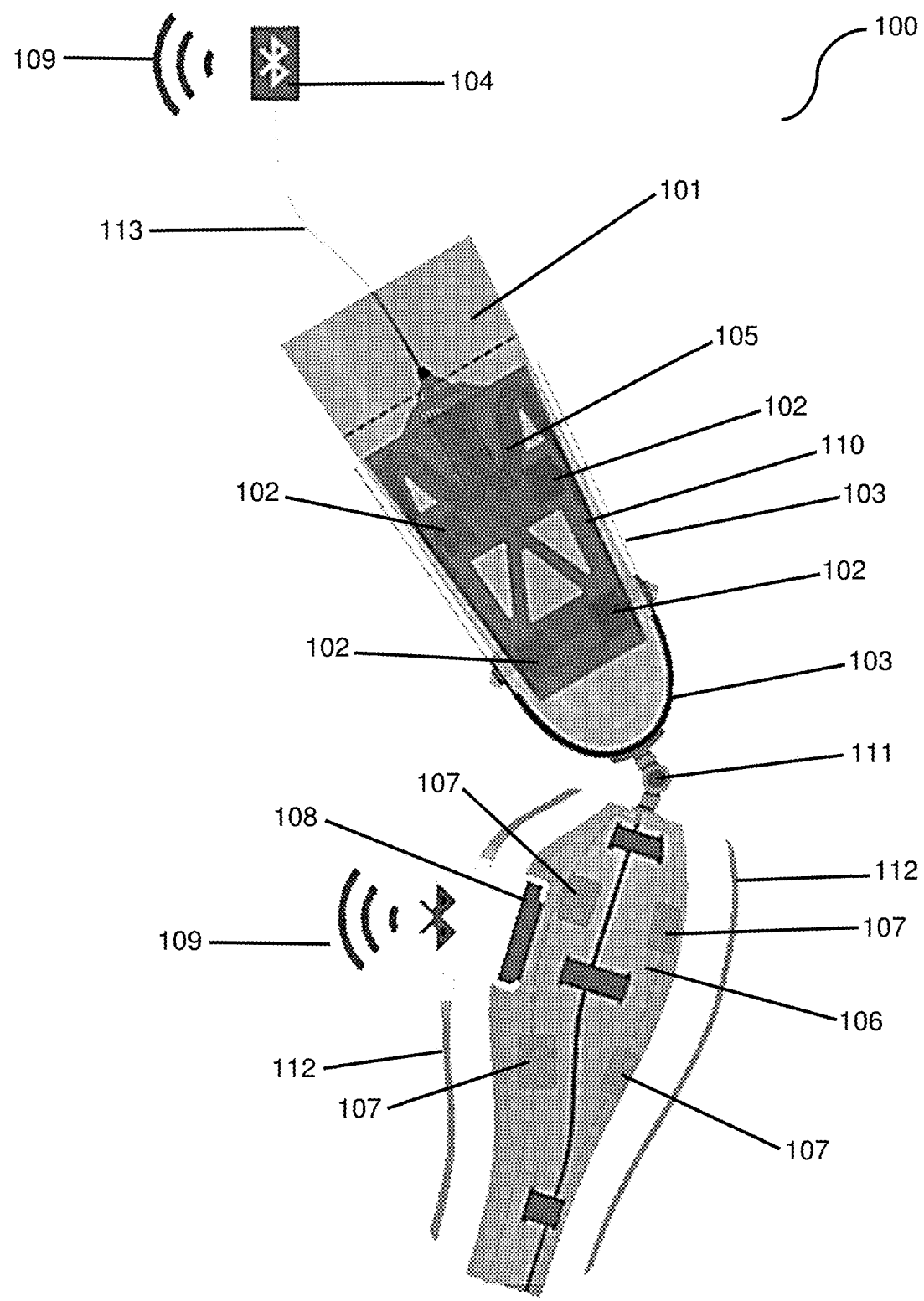
FIG. 1 depicts a system comprising a liner that comprises an array of embedded electrodes and a prosthetic cover that comprises an array of sensors.

The disclosed technology includes systems and methods to treat phantom limb syndrome by treating symptoms of phantom limb pain and increasing an amputee's proprioceptive senses of a prosthetic limb.

Following amputation of a limb, an amputee may report perception of a feeling of the missing limb, known as phantom limb sensation (PLS). In some cases, the feeling can be pain or discomfort in the missing limb, known as phantom limb pain (PLP). In extreme cases, PLP presents a debilitating condition.

Various aspects of this disclosure relate to a prosthetic cover comprising an array of sensors, which transmit signals to an array of electrodes in a liner that fits over a residual limb of an amputee. Different interactions with the prosthetic cover cause different activation of the electrodes to transmit electrical current through different areas of the residual limb and modulate neurons differently within the residual limb. As a result of the interactions with the prosthetic cover, electrical stimulation to underlying nerve fibers provide an amputee the ability to feel a stimulus. The stimuli, alone or in combination with other PLP treatment applications (e.g., artificial visualization, such as mirror therapy), can evoke a somatic sensation. As a result, the amputee may perceive the missing limb is intact and/or functional, which can decrease or resolve PLP.

In some embodiments, interactions with the prosthetic cover are any interactions, events, or modalities sensed by sensors that cause activation of the electrodes. In some embodiments, a modality is a touch modality, such as touch, force, pressure, flutter, or vibration.

Various aspects of this disclosure relate to a system for use by an amputee. In some embodiments, the system is for modulating nerve activation in a residual limb of an amputee.

In some embodiments, the system comprises a liner. In some specific embodiments, the system comprises a liner that comprises an array of electrodes. In some very specific embodiments, the system comprises a liner that comprises an embedded array of electrodes. A liner generally comprises or consists of a non-conductive polymer such as silicone.

In some embodiments, the system comprises an array of electrodes. In some specific embodiments, the system comprises an array of electrodes that are embedded in a liner. An array of electrodes may be embedded, for example, in a silicone liner. Any medical-grade electrode capable of conducting at least 30 milliamps of pulsed electrical current is generally suitable for use with the systems and methods described herein. In some specific embodiments, an electrode is suitable for transcutaneous electrical nerve stimulation. In some very specific embodiments, an electrode is a carbon rubber electrode.

The electrodes of this disclosure are generally suitable for continuous, long-term contact with human skin, which contact is optionally mediated by a conductive gel. In some embodiments, continuous, long-term contact refers to at least two hours of continuous contact. In some specific embodiments, continuous, long-term contact refers to at least twelve hours of continuous contact. In some very specific embodiments, continuous, long-term contact refers to at least 48 hours of continuous contact.

In some embodiments, the liner is a single, unified structure. In some specific embodiments, the liner is a single, unified structure in which the array of electrodes is embedded. In some very specific embodiments, the liner is a single, unified structure in which the array of electrodes and wires are embedded, wherein each electrode of the array of electrodes is connected to at least one wire such that the wires can mediate electrical communication between the array of electrodes and an electrode controller. The electrodes may comprise, for example, 2-millimeter pin connectors to create electrical communication between the electrodes and the wires. The liner may be formed, for example, by providing a substrate that comprises the electrodes and wires, inserting the substrate into a mold, and pouring liquid silicone into the mold such that the electrodes and wires become embedded in the silicone.

The liner is generally configured to receive a residual limb of an amputee. In some specific embodiments, the liner is configured to receive the residual limb such that each electrode of the array of electrodes is in electrical communication with the residual limb. A conductive gel may be applied, for example, between the electrodes of an array of electrodes and a residual limb to facilitate electrical communication between the electrodes and the residual limb.

This disclosure and the claims shall not be construed to suggest that a system of the disclosure or claims includes an amputee, a residual limb, nerve fiber, or the like unless explicit language states that the system comprises the amputee, residual limb, nerve fiber, or the like, and, if any explicit language states that the system comprises the amputee, residual limb, nerve fiber, or the like, then that explicit language shall be limited to its immediate context and shall not be used to construe other sections of this disclosure that lack the explicit language or to construe any patent claim that both matures from this disclosure and lacks the explicit language.

In some embodiments, each electrode of the array of electrodes is paired with at least two other electrodes of the array of electrodes such that, when the array of electrodes is in electrical communication with the residual limb, then each electrode can (1) transmit electrical current through the residual limb both to a first negative electrode with which the electrode is paired and, independently, to a second negative electrode with which the electrode is paired and/or (2) receive electrical current through the residual limb from both a first positive electrode with which the electrode is paired and, independently, from a second positive electrode with which the electrode is paired. In such embodiments, each electrode of the array of electrodes can transfer electrical current through and/or receive electrical current from at least two other electrodes to provide different paths of electrical current through the residual limb, for example, in response to different sensors and/or to differentially modulate nerve fibers in the residual limb.

In some embodiments, the system is configured such that when (1) two or more electrodes are activated and (2) the two or more electrodes are in electrical communication with the residual limb, then one electrode of the activated two or more electrodes transmits electrical current though the residual limb and another electrode of the activated two or more electrodes receives the electrical current that is transmitted through the residual limb. In some specific embodiments, the system is configured such that when (1) two electrodes are activated and (2) the two electrodes are in electrical communication with the residual limb, then one electrode of the activated two electrodes transmits electrical current though the residual limb and the other electrode of the activated two electrodes receives the electrical current that is transmitted through the residual limb. An electrode is activated when the electrode is transmitting or receiving electrical current.

In some embodiments, the system comprises an electrode controller in electrical communication with each electrode of the array of electrodes.

In some embodiments, the electrode controller is configured to control whether each electrode that can transmit electrical current transmits the electrical current to a negative electrode. In some embodiments, the electrode controller is configured to control whether each electrode that can receive electrical current receives the electrical current from a positive electrode. In some specific embodiments, the electrode controller is configured to control both whether each electrode that can transmit electrical current transmits the electrical current to a negative electrode and whether each electrode that can receive electrical current receives the electrical current from a positive electrode. An electrode controller can therefore control which electrodes of the array of electrodes transmit and receive electrical current, for example, in response to different sensors and/or to transmit electrical current through different regions of the residual limb.

In some embodiments, the electrode controller is configured to control whether each electrode that can transmit electrical current transmits the electrical current through the residual limb to one or both of a first negative electrode and a second negative electrode. In some embodiments, the electrode controller is configured to control whether each electrode that can receive electrical current receives the electrical current from one or both of a first positive electrode and a second positive electrode. In some specific embodiments, the electrode controller is configured to control both whether each electrode that can transmit electrical current transmits the electrical current through the residual limb to one or both of a first negative electrode and a second negative electrode and whether each electrode that can receive electrical current receives the electrical current from one or both of a first positive electrode and a second positive electrode.

In some embodiments, the electrode controller controls the electrical current transmitted or received by each electrode of the array of electrodes.

In some embodiments, the system is configured such that transmitting and receiving electrical current through the residual limb modulates nerve fibers in the residual limb. In some specific embodiments, the system is configured such that transmitting and receiving electrical current through the residual limb stimulates nerve fibers in the residual limb. In some very specific embodiments, the system is configured such that transmitting and receiving electrical current through the residual limb stimulates myelinated Aβ nerve fibers in the residual limb. In some very specific embodiments, the system is configured such that transmitting and receiving electrical current through the residual limb modulates the activation of myelinated Aδ nerve fibers in the residual limb. In some very specific embodiments, the system is configured such that transmitting and receiving electrical current through the residual limb modulates the activation of unmyelinated C nerve fibers in the residual limb.

In some embodiments, the array of electrodes is configured such that transmitting and receiving electrical current through the residual limb modulates nerve fibers in the residual limb. In some specific embodiments, the array of electrodes is configured such that transmitting and receiving electrical current through the residual limb stimulates nerve fibers in the residual limb. In some very specific embodiments, the array of electrodes is configured such that transmitting and receiving electrical current through the residual limb stimulates myelinated Aβ nerve fibers in the residual limb. In some very specific embodiments, the array of electrodes is configured such that transmitting and receiving electrical current through the residual limb modulates the activation of myelinated Aδ nerve fibers in the residual limb. In some very specific embodiments, the array of electrodes is configured such that transmitting and receiving electrical current through the residual limb modulates the activation of unmyelinated C nerve fibers in the residual limb.

In some embodiments, each electrode of the array of electrodes is configured such that transmitting and receiving electrical current through the residual limb modulates nerve fibers in the residual limb. In some specific embodiments, each electrode of the array of electrodes is configured such that transmitting and receiving electrical current through the residual limb stimulates nerve fibers in the residual limb. In some very specific embodiments, each electrode of the array of electrodes is configured such that transmitting and receiving electrical current through the residual limb stimulates myelinated Aβ nerve fibers in the residual limb. In some very specific embodiments, each electrode of the array of electrodes is configured such that transmitting and receiving electrical current through the residual limb modulates the activation of myelinated Aδ nerve fibers in the residual limb. In some very specific embodiments, each electrode of the array of electrodes is configured such that transmitting and receiving electrical current through the residual limb modulates the activation of unmyelinated C nerve fibers in the residual limb.

In some embodiments, the electrical current is pulsed electrical current.

In some embodiments, the pulsed electrical current has a pulse frequency of at least 2 and up to 200 pulses per second. In some specific embodiments, the pulsed electrical current has a pulse frequency of at least 20 and up to 180 pulses per second. In some very specific embodiments, the pulsed electrical current has a pulse frequency of at least 135 and up to 155 pulses per second.

In some embodiments, the pulsed electrical current has a pulse width of up to 400 microseconds. In some specific embodiments, the pulsed electrical current has a pulse width of up to 100 microseconds. In some very specific embodiments, the pulsed electrical current has a pulse width of up to 50 microseconds.

In some embodiments, the pulsed electrical current has an amplitude of up to 150 milliamps. In some specific embodiments, the pulsed electrical current has an amplitude of up to 100 milliamps. In some very specific embodiments, the pulsed electrical current has an amplitude of at least 10 and up to 30 milliamps.

In some embodiments, an array of electrodes comprises at least 4, 5, 6, 7, 8, 9, 10, 11, 12, 14, 16, 18, 20, 24, 28, 32, 64, 128, or 256 electrodes. In some specific embodiments, an array of electrodes comprises at least 8 and up to 512 electrodes. In some specific embodiments, an array of electrodes comprises 4, 5, 6, 7, 8, 9, 10, 11, 12, 14, 16, 18, 20, 24, 28, 32, 64, 128, 256, or 512 electrodes. In some very specific embodiments, an array of electrodes comprises 4, 5, 6, 7, 8, 9, 10, 11, 12, 14, 16, 18, 20, 24, 28, 32, 64, 128, 256, or 512 electrodes, and the system comprises a plurality of additional electrodes that are not included in the array of electrodes.

In some embodiments, the system comprises one or more electrodes that are not included in the array of electrodes. The unincluded one or more electrodes may be, for example, electrodes that are not used to transmit and/or receive electrical current to and/or from a residual limb or electrodes that a prospective infringer of one or more patent claims that mature from this disclosure might contemplate including in a system in an attempt to develop a legal theory of non-infringement.

In some embodiments, the system comprises a cover. In some specific embodiments, the system comprises a cover configured to receive a prosthesis. In some very specific embodiments, the system comprises a cover configured to receive a leg or arm prosthesis.

In some embodiments, the system lacks a prosthesis. This disclosure and the pendant claims shall not be construed to suggest that a system of the disclosure or pendant claims includes a prosthesis unless explicit language states that the system comprises the prosthesis, and, if any explicit language states that the system comprises the prosthesis, then that explicit language shall be limited to its immediate context and shall not be used to construe other sections of this disclosure that lack the explicit language or to construe any patent claim that both matures from this disclosure and lacks the explicit language.

In some embodiments, the system comprises a prosthesis.

In some embodiments, the cover is configured to overlay an outer surface of a prosthesis.

In some embodiments, the system comprises a polymer foam. In some specific embodiments, the system comprises polyurethane foam. In some very specific embodiments, the system comprises 2-part polyurethane expanding foam.

In some embodiments, the foam is configured to affix the cover to a prosthesis. In some specific embodiments, the foam is configured to fill void space between the cover and a prosthesis. In some very specific embodiments, the foam is configured to affix the cover to a prosthesis and to fill void space between the cover and the prosthesis.

In some embodiments, the foam contacts an inner surface of the cover. In some specific embodiments, the foam contacts an inner surface of the cover to affix the cover to a prosthesis. In some very specific embodiments, the foam contacts an inner surface of the cover to affix the cover to a prosthesis and to fill void space between the cover and the prosthesis.

In some embodiments, the system comprises a polymer foam, and the cover is affixed to the prosthesis with the polymer foam. In some specific embodiments, the system comprises polyurethane foam, and the cover is affixed to the prosthesis with the polyurethane foam. In some very specific embodiments, the system comprises 2-part polyurethane expanding foam, and the cover is affixed to the prosthesis with the 2-part polyurethane expanding foam. A cover may be affixed to a prosthesis, for example, by positioning the cover around the prosthesis and then inserting expanding foam between the cover and the prosthesis to fill void space between the cover and the prosthesis; the cover may thereby be affixed to different prostheses of different shapes and sizes.

In some embodiments, the foam (or components thereof) is provided in one or more containers. In some specific embodiments, the foam (or components thereof) is provided in one or more containers for use to affix the cover to a prosthesis. In some very specific embodiments, the foam (or components thereof) is provided in one or more containers for use to affix the cover to a prosthesis by inserting the foam (or components thereof) between the cover and the prosthesis to fill void space between the cover and the prosthesis.

In some embodiments, the system comprises one or more containers that contain an expandable foam. In some specific embodiments, the system comprises one or more containers that are bags that contain an expandable foam. An expandable foam may be provided, for example, in one or more containers that are bags, and the expandable foam may be expanded within the one or more bags while the one or more bags are positioned between a prosthesis and the cover to fill void space between the prosthesis and the cover and thereby affix the cover to the prosthesis. One or more bags can therefore be used, for example, to retain expandable foam within void space between a prosthesis and cover and/or to inhibit the expandable foam from entering void space within the prosthesis or cover and/or to inhibit the expandable foam from exiting the cover.

In some embodiments, the system comprises one or more straps to affix the cover to the prosthesis. Straps may be used, for example, to position the cover relative to a prosthesis prior to expanding foam within void space between the prosthesis and the cover.

In some embodiments, the cover comprises an array of sensors.

In some embodiments, each sensor of the array of sensors is configured to sense at least one modality (e.g., one or both of force and pressure). Each sensor may be, for example, a force sensing resistor.

In some embodiments, each sensor of the array of sensors comprises a resistor that is configured to sense at least one modality (e.g., one or both of force and pressure). The precise type of modality sensor is not limiting.

In some embodiments, the system is configured such that the amplitude of the electrical current transmitted and received by electrodes of the array of electrodes through the residual limb directly correlates with a modality (e.g., pressure or force) sensed by a sensor, for example, such that increased modality (e.g., increased pressure or increased force) correlates with increased amplitude.

In some embodiments, the array of electrodes is in communication with the array of sensors such that two or more electrodes are activated in response to sensing by one or more sensors. In some specific embodiments, the array of electrodes is in communication with the array of sensors such that two electrodes are activated in response to sensing by one sensor.

In some embodiments, each sensor corresponds to at least two electrodes. In some specific embodiments, each sensor corresponds to two electrodes.

In some embodiments, each electrode corresponds to at least one sensor. In some specific embodiments, each electrode corresponds to at least two sensors.

A sensor corresponds to an electrode if the sensor is in communication with the electrode such that the electrode will transmit or receive electrical current to or from the residual limb when both the sensor senses a modality (e.g., force or pressure) and the electrode is in electrical communication with the residual limb.

An electrode corresponds to a sensor if the sensor is in communication with the electrode such that the electrode will transmit or receive electrical current to or from the residual limb when both the sensor senses a modality (e.g., force or pressure) and the electrode is in electrical communication with the residual limb.

In some embodiments, the array of sensors has a sensor three-dimensional configuration relative to the cover.

In some embodiments, the array of sensors has a sensor three-dimensional configuration relative to an outer surface of a prosthesis when the cover is attached to the outer surface of the prosthesis.

In some embodiments, the array of electrodes has an electrode three-dimensional configuration relative to the liner.

In some embodiments, the array of electrodes has an electrode three-dimensional configuration relative to the residual limb when each of the electrodes is in electrical communication with the residual limb.

In some embodiments, each sensor has a sensor relative position in the sensor three-dimensional configuration relative to every other sensor of the array of sensors; each electrode has an electrode relative position in the electrode three-dimensional configuration relative to every other electrode of the array of electrodes; the system comprises sensor-electrode pairs that each consist of one or more sensors and two or more electrodes, which sensor(s) and electrodes correspond to each other; and the sensor relative position of each sensor of a sensor-electrode pair within the sensor three-dimensional configuration correlates with the electrode relative position of each electrode of the same sensor-electrode pair within the electrode three-dimensional configuration. In some specific embodiments, the system comprises sensor-electrode pairs that each comprise one sensor and two electrodes, which sensor and electrodes correspond to each other.

A sensor relative position correlates with an electrode relative position, for example, when (a) the sensors comprise an anterior-proximal sensor, an anterior-distal sensor, a lateral-proximal sensor, a lateral-distal sensor, a posterior-proximal sensor, a posterior-distal sensor, a medial-proximal sensor, and a medial-distal sensor; (b) the electrodes comprise an anterior-proximal electrode, an anterior-distal electrode, a lateral-proximal electrode, a lateral-distal electrode, a posterior-proximal electrode, a posterior-distal electrode, a medial-proximal electrode, and a medial-distal electrode; (c) the sensor-electrode pairs comprise each of an anterior-proximal pair that comprises the anterior-proximal sensor and the anterior-proximal electrode, an anterior-distal pair that comprises the anterior-distal sensor and the anterior-distal electrode, a lateral-proximal pair that comprises the lateral-proximal sensor and the lateral-proximal electrode, a lateral-distal pair that comprises the lateral-distal sensor and the lateral-distal electrode, a posterior-proximal pair that comprises the posterior-proximal sensor and the posterior-proximal electrode, a posterior-distal pair that comprises the posterior-distal sensor and the posterior-distal electrode, a medial-proximal pair that comprises the medial-proximal sensor and the medial-proximal electrode, and a medial-distal pair that comprises the medial-distal sensor and the medial-distal electrode; (d) the sensor relative position of the anterior-proximal sensor is (1) closer to the anterior-distal sensor than both the lateral-distal sensor and the medial-distal sensor, (2) closer to both the lateral-distal sensor and the medial-distal sensor than the posterior-distal sensor, (3) closer to both the lateral-proximal sensor and the medial-proximal sensor than the posterior-proximal sensor, and (4) closer to the posterior-proximal sensor than the posterior-distal sensor; (e) the electrode relative position of the anterior-proximal electrode is (1) closer to the anterior-distal electrode than both the lateral-distal electrode and the medial-distal electrode, (2) closer to both the lateral-distal electrode and the medial-distal electrode than the posterior-distal electrode, (3) closer to both the lateral-proximal electrode and the medial-proximal electrode than the posterior-proximal electrode, and (4) closer to the posterior-proximal electrode than the posterior-distal electrode; (f) the sensor relative position of the anterior-distal sensor is (1) closer to the anterior-proximal sensor than both the lateral-proximal sensor and the medial-proximal sensor, (2) closer to both the lateral-proximal sensor and the medial-proximal sensor than the posterior-proximal sensor, (3) closer to both the lateral-distal sensor and the medial-distal sensor than the posterior-distal sensor, and (4) closer to the posterior-distal sensor than the posterior-proximal sensor; (g) the electrode relative position of the anterior-distal electrode is (1) closer to the anterior-proximal electrode than both the lateral-proximal electrode and the medial-proximal electrode, (2) closer to both the lateral-proximal electrode and the medial-proximal electrode than the posterior-proximal electrode, (3) closer to both the lateral-distal electrode and the medial-distal electrode than the posterior-distal electrode, and (4) closer to the posterior-distal electrode than the posterior-proximal electrode; (h) the sensor relative position of the medial-proximal sensor is (1) closer to the medial-distal sensor than both the anterior-distal sensor and the posterior-distal sensor, (2) closer to both the anterior-distal sensor and the posterior-distal sensor than the lateral-distal sensor, (3) closer to both the anterior-proximal sensor and the posterior-proximal sensor than the lateral-proximal sensor, and (4) closer to the lateral-proximal sensor than the lateral-distal sensor; (i) the electrode relative position of the medial-proximal electrode is (1) closer to the medial-distal electrode than both the anterior-distal electrode and the posterior-distal electrode, (2) closer to both the anterior-distal electrode and the posterior-distal electrode than the lateral-distal electrode, (3) closer to both the anterior-proximal electrode and the posterior-proximal electrode than the lateral-proximal electrode, and (4) closer to the lateral-proximal electrode than the lateral-distal electrode; (j) the sensor relative position of the medial-distal sensor is (1) closer to the medial-proximal sensor than both the anterior-proximal sensor and the posterior-proximal sensor, (2) closer to both the anterior-proximal sensor and the posterior-proximal sensor than the lateral-proximal sensor, (3) closer to both the anterior-distal sensor and the posterior-distal sensor than the lateral-distal sensor, and (4) closer to the lateral-distal sensor than the lateral-proximal sensor; (k) the electrode relative position of the medial-distal electrode is (1) closer to the medial-proximal electrode than both the anterior-proximal electrode and the posterior-proximal electrode, (2) closer to both the anterior-proximal electrode and the posterior-proximal electrode than the lateral-proximal electrode, (3) closer to both the anterior-distal electrode and the posterior-distal electrode than the lateral-distal electrode, and (4) closer to the lateral-distal electrode than the lateral-proximal electrode; (l) the sensor relative position of the posterior-proximal sensor is (1) closer to the posterior-distal sensor than both the lateral-distal sensor and the medial-distal sensor, (2) closer to both the lateral-distal sensor and the medial-distal sensor than the anterior-distal sensor, (3) closer to both the lateral-proximal sensor and the medial-proximal sensor than the anterior-proximal sensor, and (4) closer to the anterior-proximal sensor than the anterior-distal sensor; (m) the electrode relative position of the posterior-proximal electrode is (1) closer to the posterior-distal electrode than both the lateral-distal electrode and the medial-distal electrode, (2) closer to both the lateral-distal electrode and the medial-distal electrode than the anterior-distal electrode, (3) closer to both the lateral-proximal electrode and the medial-proximal electrode than the anterior-proximal electrode, and (4) closer to the anterior-proximal electrode than the anterior-distal electrode; (n) the sensor relative position of the posterior-distal sensor is (1) closer to the posterior-proximal sensor than both the lateral-proximal sensor and the medial-proximal sensor, (2) closer to both the lateral-proximal sensor and the medial-proximal sensor than the anterior-proximal sensor, (3) closer to both the lateral-distal sensor and the medial-distal sensor than the anterior-distal sensor, and (4) closer to the anterior-distal sensor than the anterior-proximal sensor; (o) the electrode relative position of the posterior-distal electrode is (1) closer to the posterior-proximal electrode than both the lateral-proximal electrode and the medial-proximal electrode, (2) closer to both the lateral-proximal electrode and the medial-proximal electrode than the anterior-proximal electrode, (3) closer to both the lateral-distal electrode and the medial-distal electrode than the anterior-distal electrode, and (4) closer to the anterior-distal electrode than the anterior-proximal electrode; (p) the sensor relative position of the lateral-proximal sensor is (1) closer to the lateral-distal sensor than both the anterior-distal sensor and the posterior-distal sensor, (2) closer to both the anterior-distal sensor and the posterior-distal sensor than the medial-distal sensor, (3) closer to both the anterior-proximal sensor and the posterior-proximal sensor than the medial-proximal sensor, and (4) closer to the medial-proximal sensor than the medial-distal sensor; (q) the electrode relative position of the lateral-proximal electrode is (1) closer to the lateral-distal electrode than both the anterior-distal electrode and the posterior-distal electrode, (2) closer to both the anterior-distal electrode and the posterior-distal electrode than the medial-distal electrode, (3) closer to both the anterior-proximal electrode and the posterior-proximal electrode than the medial-proximal electrode, and (4) closer to the medial-proximal electrode than the medial-distal electrode; (r) the sensor relative position of the lateral-distal sensor is (1) closer to the lateral-proximal sensor than both the anterior-proximal sensor and the posterior-proximal sensor, (2) closer to both the anterior-proximal sensor and the posterior-proximal sensor than the medial-proximal sensor, (3) closer to both the anterior-distal sensor and the posterior-distal sensor than the medial-distal sensor, and (4) closer to the medial-distal sensor than the medial-proximal sensor; and (s) the electrode relative position of the lateral-distal electrode is (1) closer to the lateral-proximal electrode than both the anterior-proximal electrode and the posterior-proximal electrode, (2) closer to both the anterior-proximal electrode and the posterior-proximal electrode than the medial-proximal electrode, (3) closer to both the anterior-distal electrode and the posterior-distal electrode than the medial-distal electrode, and (4) closer to the medial-distal electrode than the medial-proximal electrode.

The foregoing paragraph sets forth an illustrative correlation between each sensor relative position of a sensor three-dimensional configuration and each electrode relative position of an electrode three-dimensional configuration. The sensor relative positions of a different array of sensors may correlate with the electrode relative positions of a different array of electrodes with an analogous-yet-distinct correlation, for example, to allow for different patterns of sensors and/or electrodes. A sensor relative position typically correlates with an electrode relative position, for example, such that an anterior sensor activates an anterior electrode, a posterior sensor activates a posterior electrode, a medial sensor activates a medial electrode, and a lateral sensor activates a lateral electrode. Pressing the front of a lower leg prosthesis would therefore transmit electrical current through the front of an upper residual leg, and pressing the back of a lower leg prosthesis would therefore transmit electrical current through the back of an upper residual leg. Other patterns are nevertheless compatible with the systems of this disclosure. Without limiting this specification or any patent claim that matures from this disclosure, correlation between the relative positions of the sensors and paired electrodes may facilitate topographic mapping and more-effectively treat phantom limb syndrome.

In some embodiments, the sensor three-dimensional configuration defines a sensor surface; the electrode three-dimensional configuration defines an electrode surface; and closeness is measured along the sensor surface and the electrode surface and not in Cartesian space. In some embodiments, the sensor surface is a surface of the cover. In some specific embodiments, the sensor surface is an outer surface of the cover. In some embodiments, the electrode surface is a surface of the liner. In some specific embodiments, the electrode surface is an inner surface of the liner.

The adjectives anterior, lateral, posterior, medial, distal, and proximal indicate (1) sensor relative positions of sensors relative to both a cover (or prosthesis) and other sensors and also (2) electrode relative positions of electrodes relative to both a liner (or residual limb) and other electrodes. An anterior-distal sensor is closer to the front of a cover (or prosthesis), for example, than lateral-distal, posterior-distal, and medial-distal sensors. An anterior-distal sensor is lower on a leg or arm prosthetic cover (or leg or arm prosthesis), for example, than an anterior-proximal sensor.

The terms anterior-proximal sensor, anterior-distal sensor, lateral-proximal sensor, lateral-distal sensor, posterior-proximal sensor, posterior-distal sensor, medial-proximal sensor, medial-distal sensor, and the like shall (1) only be construed to identify sensor relative positions, (2) shall not be construed to imply a sensor three-dimensional configuration such as by implying a regular grid, and (3) shall not to be construed to imply the existence or absence of any other sensor of an array of sensors.

The terms anterior-proximal electrode, anterior-distal electrode, lateral-proximal electrode, lateral-distal electrode, posterior-proximal electrode, posterior-distal electrode, medial-proximal electrode, medial-distal electrode, and the like shall (1) only be construed to identify electrode relative positions, (2) shall not be construed to imply an electrode three-dimensional configuration such as by implying a regular grid, and (3) shall not to be construed to imply the existence or absence of any other electrode of an array of electrodes.

In some embodiments, each sensor corresponds to exactly two electrodes, and each sensor-electrode pair consists of (1) a sensor and (2) two electrodes that correspond to the sensor. In some specific embodiments, each sensor corresponds to exactly two electrodes, and each sensor-electrode pair consists of (1) a sensor and (2) two electrodes that correspond to the sensor, wherein one of the two electrodes is a positive electrode that is configured to transmit electrical current and the other of the two electrodes is a negative electrode that is configured to receive the electrical current from the positive electrode. In some very specific embodiments, each sensor corresponds to exactly two electrodes, and each sensor-electrode pair consists of (1) a sensor and (2) two electrodes that correspond to the sensor, wherein one of the two electrodes is a positive electrode that is configured to transmit electrical current to a residual limb and the other of the two electrodes is a negative electrode that is configured to receive the electrical current from the positive electrode through the residual limb.

In some embodiments, the array of electrodes comprises at least one ring of electrodes, wherein a ring of electrodes consists of four or more electrodes that are each paired with exactly two other electrodes of the ring. In some specific embodiments, the array of electrodes comprises at least two, three, four, five, or six rings of electrodes. In some very specific embodiments, the array of electrodes comprises at least eight electrodes and at least six rings of electrodes. An anterior-proximal electrode, anterior-distal electrode, lateral-proximal electrode, and lateral-distal electrode are a ring of electrodes, for example, if the anterior-proximal and lateral-distal electrodes are each paired with the anterior-distal and lateral-proximal electrodes.

In some embodiments, at least one of the rings of electrodes are configured to encircle the residual limb. An anterior-distal electrode, lateral-distal electrode, posterior-distal electrode, and medial-distal electrode are a ring of electrodes configured to encircle the residual limb, for example, if the anterior-distal and posterior-distal electrodes are each paired with the lateral-distal and medial-distal electrodes. In some specific embodiments, at least two of the rings of electrodes are configured to encircle the residual limb.

In some embodiments, the array of sensors comprises one, two, three, four, five, six, seven, or each of an anterior-proximal sensor, an anterior-distal sensor, a lateral-proximal sensor, a lateral-distal sensor, a posterior-proximal sensor, a posterior-distal sensor, a medial-proximal sensor, and a medial-distal sensor.

In some embodiments, the array of electrodes comprises one, two, three, four, five, six, seven, or each of an anterior-proximal electrode, an anterior-distal electrode, a lateral-proximal electrode, a lateral-distal electrode, a posterior-proximal electrode, a posterior-distal electrode, a medial-proximal electrode, and a medial-distal electrode.

In some embodiments, the sensor-electrode pairs comprise one, two, three, four, five, six, seven, or each of an anterior-proximal pair that comprises the anterior-proximal sensor and the anterior-proximal electrode, an anterior-distal pair that comprises the anterior-distal sensor and the anterior-distal electrode, a lateral-proximal pair that comprises the lateral-proximal sensor and the lateral-proximal electrode, a lateral-distal pair that comprises the lateral-distal sensor and the lateral-distal electrode, a posterior-proximal pair that comprises the posterior-proximal sensor and the posterior-proximal electrode, a posterior-distal pair that comprises the posterior-distal sensor and the posterior-distal electrode, a medial-proximal pair that comprises the medial-proximal sensor and the medial-proximal electrode, and a medial-distal pair that comprises the medial-distal sensor and the medial-distal electrode. Each of the sensor-electrode pairs identified in the preceding sentence also include an additional electrode; the anterior-proximal pair also comprises, for example, one or more of a second anterior-proximal electrode, the anterior-distal electrode, the lateral-proximal electrode, the medial-proximal electrode, or an entirely different electrode.

In some embodiments, each sensor of the array of sensors is in communication with two or more electrodes of the array of electrodes such that the two or more electrodes are configured to transmit and receive electrical current through the residual limb when each of (1) the sensor senses force or pressure; (2) the two or more electrodes are in electrical communication with the residual limb; and (3) the prosthesis is detached from the residual limb. Such configurations allow an amputee to transmit electrical current through his or her residual limb, optionally to treat symptoms of phantom limb syndrome, when the amputee is not wearing a prosthesis with the cover, for example, after the amputee has removed such a prosthesis to sleep.

In some embodiments, an array of sensors comprises at least 4, 5, 6, 7, 8, 9, 10, 11, 12, 14, 16, 18, 20, 24, 28, or 32 sensors. In some specific embodiments, an array of sensors comprises at least 4 and up to 128 sensors. In some specific embodiments, an array of sensors comprises 4, 5, 6, 7, 8, 9, 10, 11, 12, 14, 16, 18, 20, 24, 28, 32, 64, or 128 sensors. In some very specific embodiments, an array of sensors comprises 4, 5, 6, 7, 8, 9, 10, 11, 12, 14, 16, 18, 20, 24, 28, 32, 64, or 128 sensors, and the system comprises a plurality of additional sensors that are not included in the array of sensors.

In some embodiments, the system comprises one or more sensors that are not included in the array of sensors. The unincluded one or more sensors may be, for example, sensors that are not used to detect force or pressure or sensors that a prospective infringer of one or more patent claims that mature from this disclosure might contemplate including in a system in an attempt to develop a legal theory of non-infringement.

In some embodiments, the system comprises a controller, wherein the controller is in communication with the array of electrodes such that the controller can bypass the array of sensors to cause each electrode of the array of electrodes to transmit or receive electrical current to or from a residual limb of an amputee when the electrode is in electrical communication with the residual limb. Such a controller can allow an amputee to transmit electrical current through his or her residual limb when the amputee is not wearing a prosthesis with the cover, for example, after the amputee has removed such a prosthesis to sleep. A controller can also allow an amputee to run programs that specifically treat phantom limb syndrome. An amputee might develop a specific pattern of transmitting electrical current through his or her residual limb that is particularly efficacious at treating phantom limb syndrome, the system might track an amputee's use of the system and develop a specific pattern that displays a high probability of efficaciously treating phantom limb syndrome, or crowd-sourced use records from a plurality of amputees or other data might identify a specific pattern that displays a high probability of efficaciously treating phantom limb syndrome, and a program on a controller can drive the array of electrodes to implement the specific pattern. Such a controller may optionally be an electrode controller or a secondary controller as described herein.

In some embodiments, the system comprises a secondary controller in wireless communication with the array of electrodes such that the secondary controller can bypass the array of sensors to cause each electrode of the array of electrodes to transmit or receive electrical current to or from the residual limb when the array of electrodes is in electrical communication with the residual limb.

In some embodiments, the secondary controller is a computing device. In some specific embodiments, the secondary controller is a mobile computing device. In some very specific embodiments, the secondary controller is a cellphone.

In some embodiments, the secondary controller is in wireless communication with the array of electrodes. In some specific embodiments, the secondary controller is in wireless communication with an electrode controller. In some very specific embodiments, the secondary controller is in wireless communication with an electrode controller that controls the array of electrodes.

In some embodiments, the wireless communication is mediated by one or both of a Bluetooth or Wi-Fi connection between the secondary controller and the array of electrodes. In some specific embodiments, the wireless communication is mediated by one or both of a Bluetooth or Wi-Fi connection between the secondary controller and the array of electrodes, which is mediated by an electrode controller that controls the array of electrodes.

In some embodiments, the secondary controller is in wireless communication with the electrode controller.

In some embodiments, the cover is configured to attach to outer surfaces of different prostheses that have a variety of different shapes, and the cover is configured to adapt to the variety of different shapes such that each sensor relative position remains constant for different shapes. In some specific embodiments, the cover is configured to attach to outer surfaces of different prostheses that have a variety of different shapes, and the cover is configured to adapt to the variety of different shapes such that each sensor three-dimensional configuration remains constant for different shapes.

In some embodiments, the cover has a shape of a missing body part. In some specific embodiments, the cover has a shape of a missing body part, and the sensor three-dimensional configuration comprises the shape of the missing body part. Without limiting this specification or any patent claim that matures from this disclosure, a cover that has a shape of a missing part and a sensor three-dimensional configuration that comprises the shape more favorably induces neuroplasticity in the somatosensory cortex of the brain of an amputee than other shapes, which more efficaciously treats phantom limb syndrome.

In some embodiments, the system lacks any sensor ability to sense a relative position of a prosthesis. In some specific embodiments, the array of sensors is generally configured to sense pressure and/or force from touch, and the array of sensors is not generally configured to sense the position or performance of a prosthesis.

In some embodiments, the system lacks any mechanical capability to move a prosthesis. In some specific embodiments, the system is generally unrelated to the mechanical properties of a prosthesis, for example, to support movement, positioning, or load.

In some embodiments, the system lacks any structural ability to support bodyweight of an amputee. In some specific embodiments, the system is generally unrelated to the structural properties of a prosthesis, for example, to support movement, positioning, or load.

FIG. 1 depicts a system 100, which comprises a liner 101 that comprises an embedded array of electrodes 102. The liner 101 receives a residual limb (not shown) such that the liner 101 fits underneath a region of a prosthesis 103 that also receives the residual limb. Each electrode 102 of the array of electrodes 102 is in electrical communication with an electrode controller 104, which electrical communication is mediated by wires 105 that are also embedded in the liner 101. FIG. 1 depicts a system 100, which also comprises a cover 106 that comprises an embedded array of sensors 107. The cover 106 fits over a region of the prosthesis 103 that replaces a missing limb and is optionally attached to the prosthesis 103 with a polymer foam (not shown) that fills void space between the cover 106 and the prosthesis 103. The sensors 107 are in communication with a sensor controller 108 that interfaces with the electrode controller 104.

FIG. 1 depicts a wireless, Bluetooth-mediated interface 109 between the sensor controller 108 and the electrode controller 104. The wireless, Bluetooth-mediated interface 109 between the sensor controller 108 and the electrode controller 104 allows amputees to contact the sensors 107 to activate electrodes 102 of the array of electrodes 102 to stimulate their residual limbs even when an amputee is not wearing the prosthetic 103 and cover 106, for example, such as when the amputee has removed the prosthetic 103 to sleep. In other embodiments, the system 100 lacks a sensor controller 108, and sensors 107 are connected directly to the electrode controller 104.

The liner 101 of FIG. 1 comprises a substrate 110 that houses the embedded array of electrodes 102. Also shown in FIG. 1 is a joint 111 of the prosthesis 103, an outer layer 112 of the cover 106, which outer layer 112 is shown in an exploded view, and sheathing 113 that bundles wires 105 that exit the liner 101.

Figure 2:
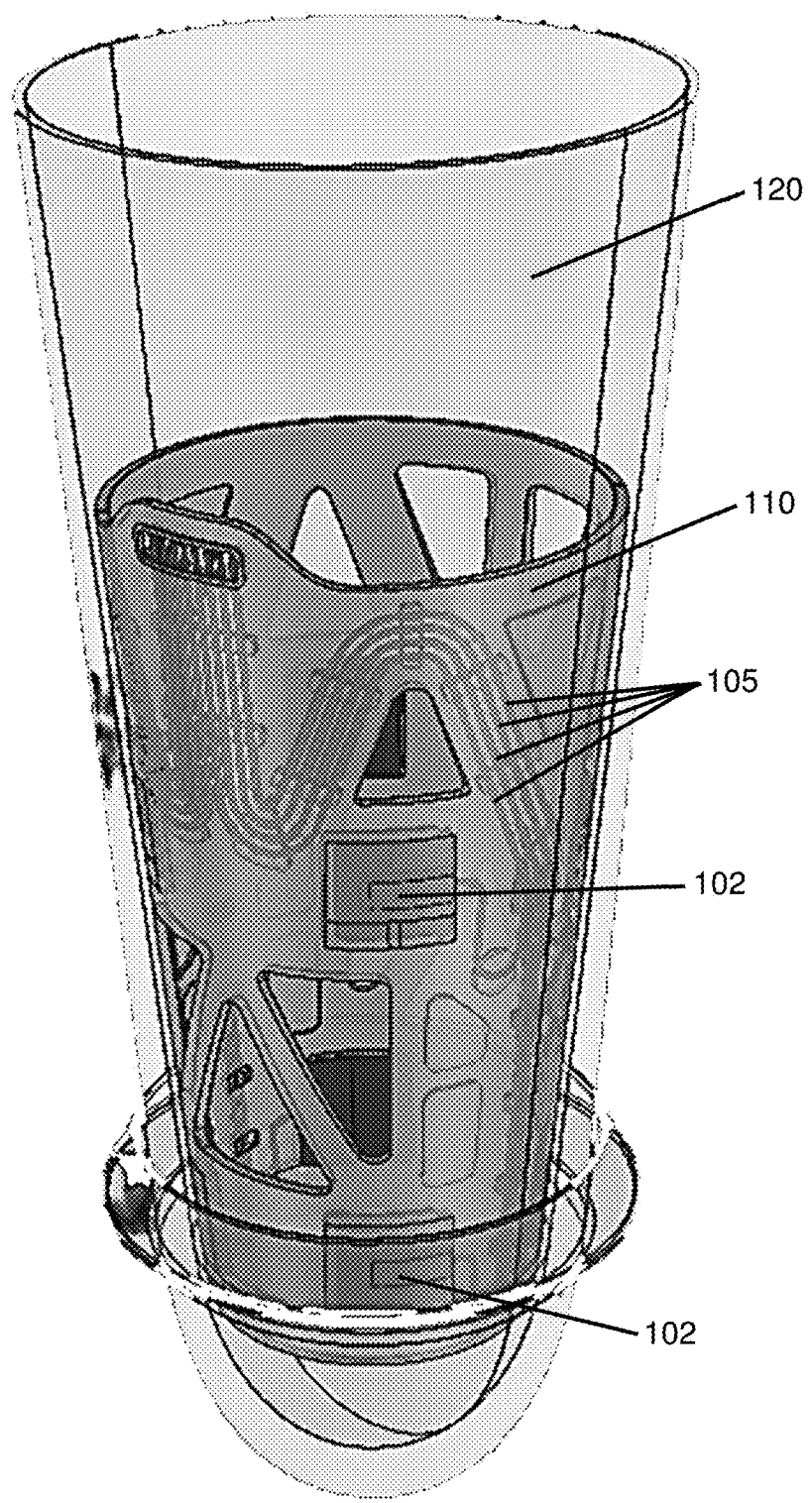
FIG. 2 depicts a substrate and a mold for manufacturing a liner.

FIG. 2 depicts a substrate 110 with an embedded array of electrodes 102 and embedded wires 105. The substrate 110 is positioned within a mold 120. Liquid silicone (not shown) may be poured into the mold 120 to form a liner (not shown) that comprises the embedded array of electrodes 102 and embedded wires 105.

Figure 3:
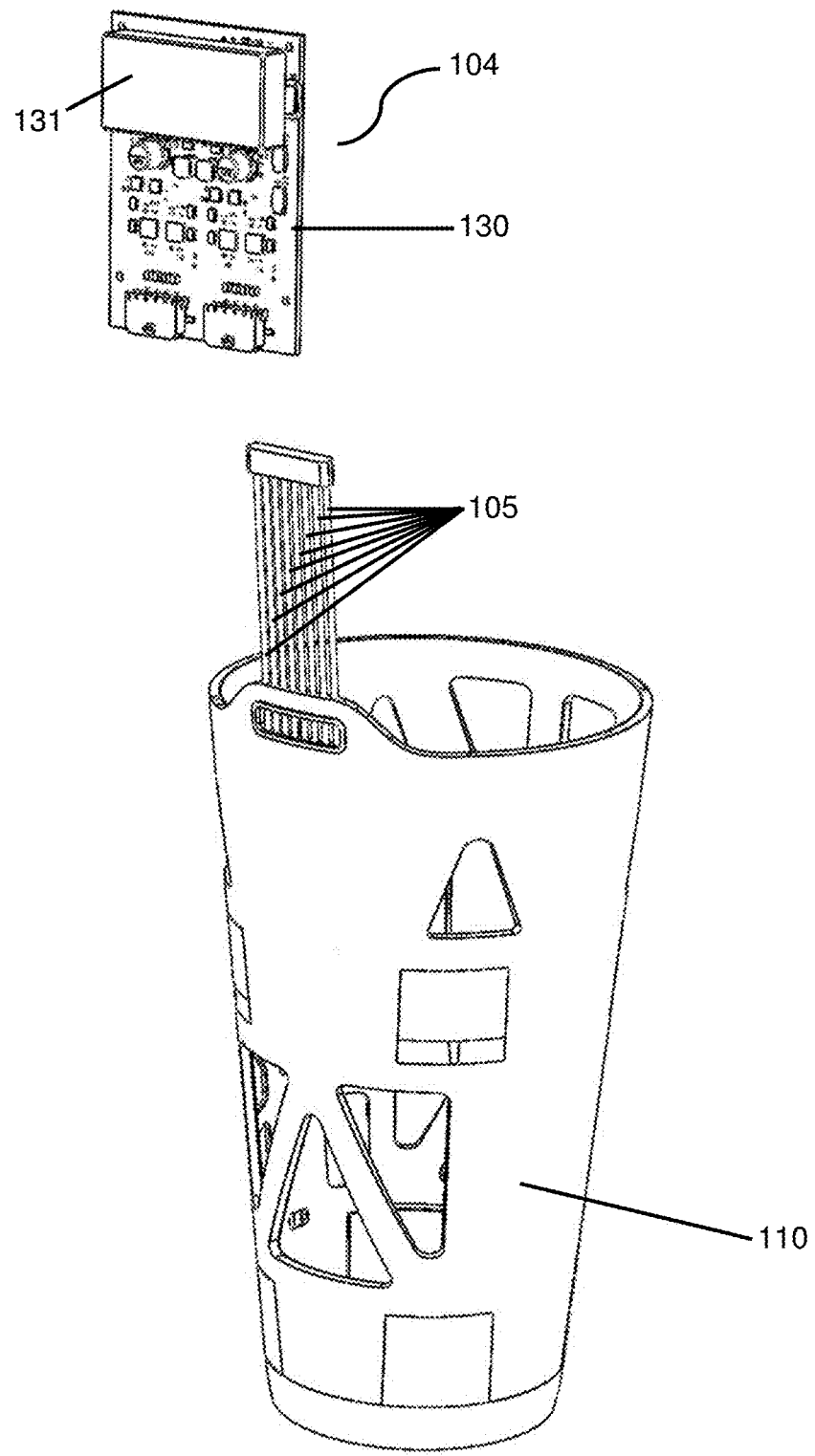
FIG. 3 depicts a substrate and an electrode controller.

FIG. 3 depicts a substrate 110 with an embedded array of electrodes (not shown) and embedded wires 105. FIG. 3 also depicts an electrode controller 104, which comprises a printed circuit board assembly 130 and a battery 131 in electrical communication with the printed circuit board assembly 130. When the electrode controller 104 is in electrical communication with the embedded wires 105, then a microprocessor (not shown) of the printed circuit board assembly 130 of the electrode controller 104 controls the transmission of electrical current between the battery 131 and the embedded wires 105 to control whether an electrode of the array of electrodes will transmit electrical current, which the electrode receives from the battery 131, and whether an electrode of the array of electrodes will receive electrical current, which the electrode transmits to the battery 131.

Figure 4:
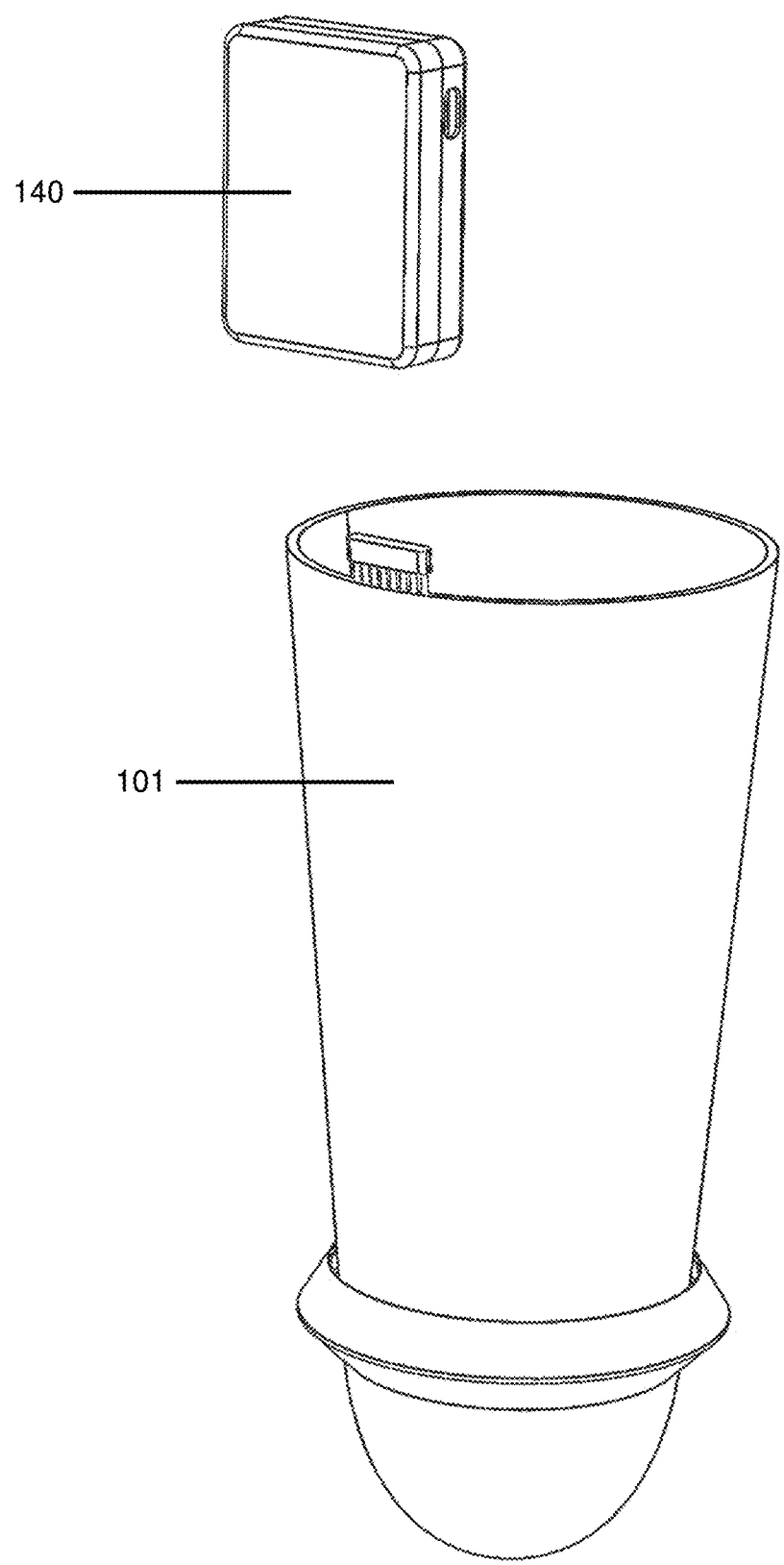
FIG. 4 depicts a liner and a housing that houses an electrode controller.

FIG. 4 depicts a liner 101 that comprises the substrate (not shown) of FIG. 3 and an electrode controller housing 140 that houses the electrode controller (not shown) of FIG. 3.

Figure 5:
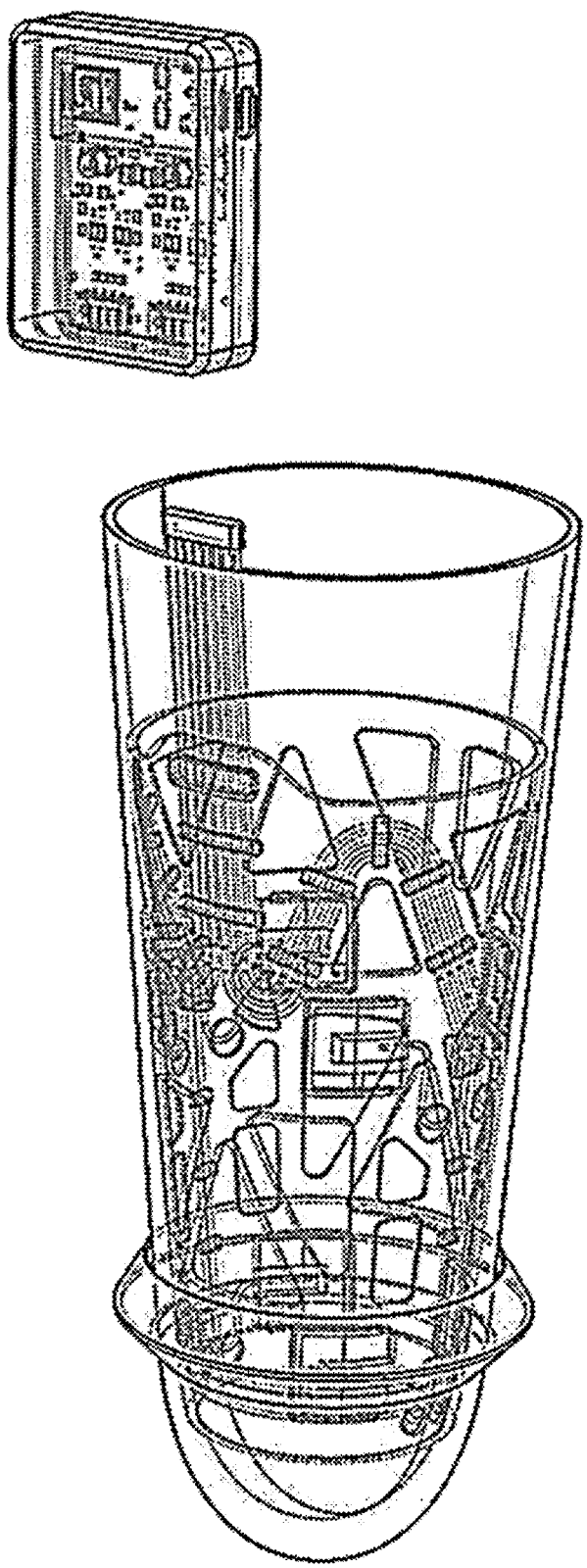
FIG. 5 depicts the liner and housing of FIG. 4 with partial transparency such that a substrate and electrode controller are visible.

FIG. 5 depicts the liner 101 and electrode controller housing 140 of FIG. 4 with partial transparency such that the substrate 110 and electrode controller 104 are visible.

Figure 6:
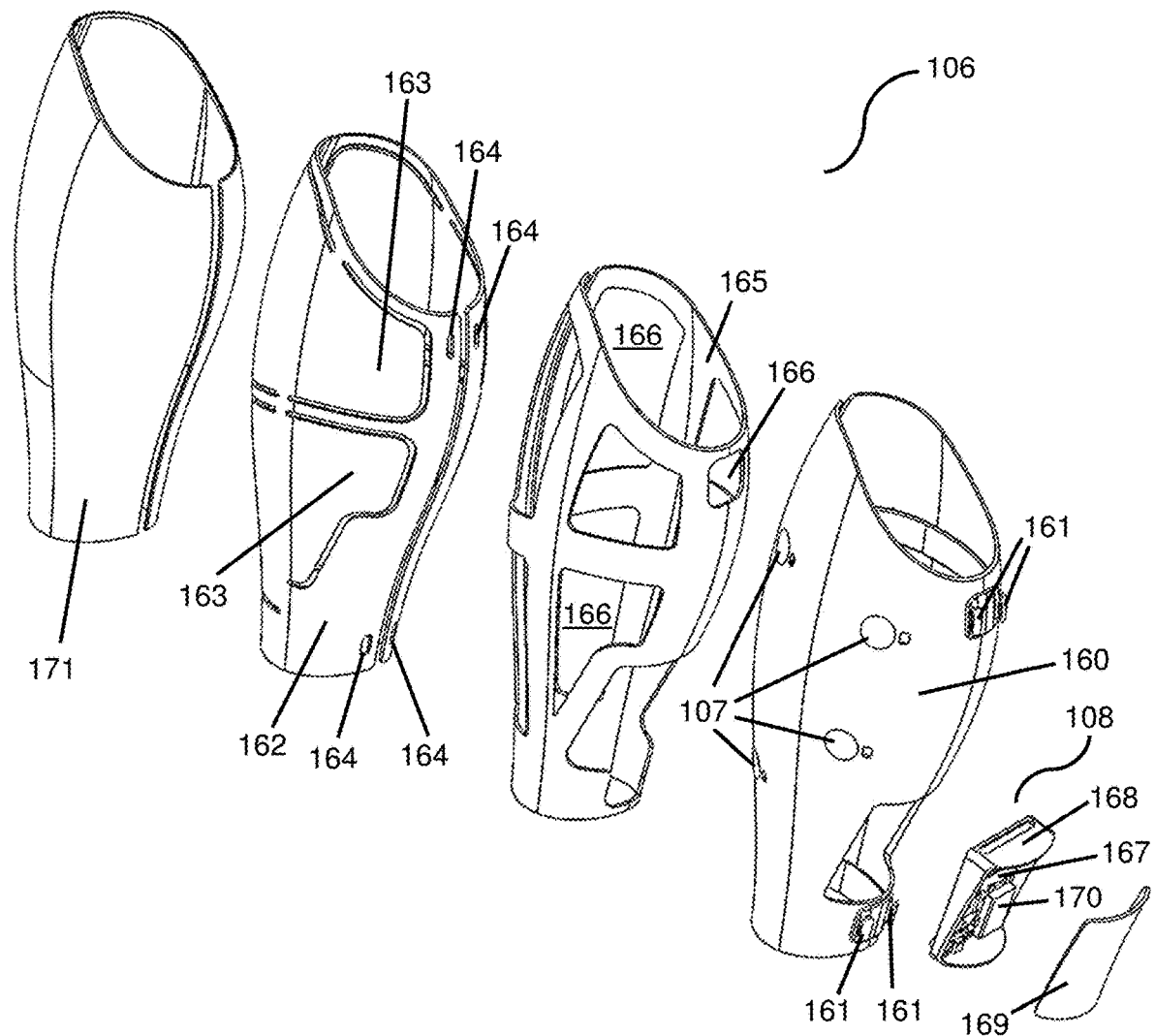
FIG. 6 depicts an exploded view of a cover configured to fit over a prosthesis.

FIG. 6 depicts an exploded view of a cover 106, which comprises sensors 107. The cover 106 comprises an inner layer 160, which is depicted with embedded sensors 107 that are configured to sense a modality (e.g., force or pressure). The inner layer 160 may be manufactured, for example, from plastic. The inner layer 160 optionally comprises one or more tabs 161 or other attachment feature to receive an outer layer 162. The outer layer 162 may be manufactured, for example, from plastic. The outer layer 162 may optionally have actuators 163, each of which is configured to press against one or more sensors 107. Each actuator 163 may be configured, for example, as a flex panel that has a larger surface area than any of the sensors 107 such that depressing any portion of an actuator 163 transduces a modality (e.g., force or pressure) to one or more of the smaller sensors 107. The outer layer 162 optionally comprises one or more slots 164 or other attachment feature to receive the inner layer 160. As shown in FIG. 6, the outer layer 162 comprises four slots 164 that are shaped to receive four tabs 161 of the inner layer 160 to attach the outer layer 162 and the inner layer 160. A mechanical attachment feature, such as a tab, may include a detent, barb, or other catch or clamp feature to inhibit detachment of the inner layer 160 and the outer layer 162.

The cover 106 may optionally comprise a spacer 165 between the inner layer 160 and the outer layer 162. The spacer 165 may comprise, for example, foam. The spacer 165 may include one or more voids 166. The one or more voids 166 can allow, for example, an actuator 163 to contact a sensor 107. The one or more voids 166 can also allow, for example, an attachment feature such as the one or more tabs 161 and the one or more slots 164 to attach the inner layer 160 and the outer layer 162.

The cover 106 may optionally include a sensor controller 108. A sensor controller 108 typically comprises a printed circuit board assembly 167 that comprises an interface and a microprocessor. The microprocessor is configured, for example, to receive signals from the sensors 107 and direct the interface to transmit a corresponding signal to the array of electrodes or a controller thereof. The interface may be, for example, a wireless interface such as a combined Wifi Bluetooth chip. The precise type of interface is not limiting and generally depends upon market factors including the manufacturer suggested retail price of the system. The controller 108 typically comprises a controller housing 168, which may optionally comprise an access panel 169 to allow access to the printed circuit board assembly 167. A sensor controller 108 typically either comprises or is otherwise in electrical communication with a power source, which is typically a battery 170.

In some embodiments, a cover lacks a dedicated sensor controller (not shown). A system may comprise, for example, a hardwired interface between a cover and a liner such that a sensor controller is unnecessary.

The cover 106 may optionally comprise an outer surface 171, which may comprise, for example, foam and/or a favorable texture for physical interaction with actuators 163.

Figure 7:
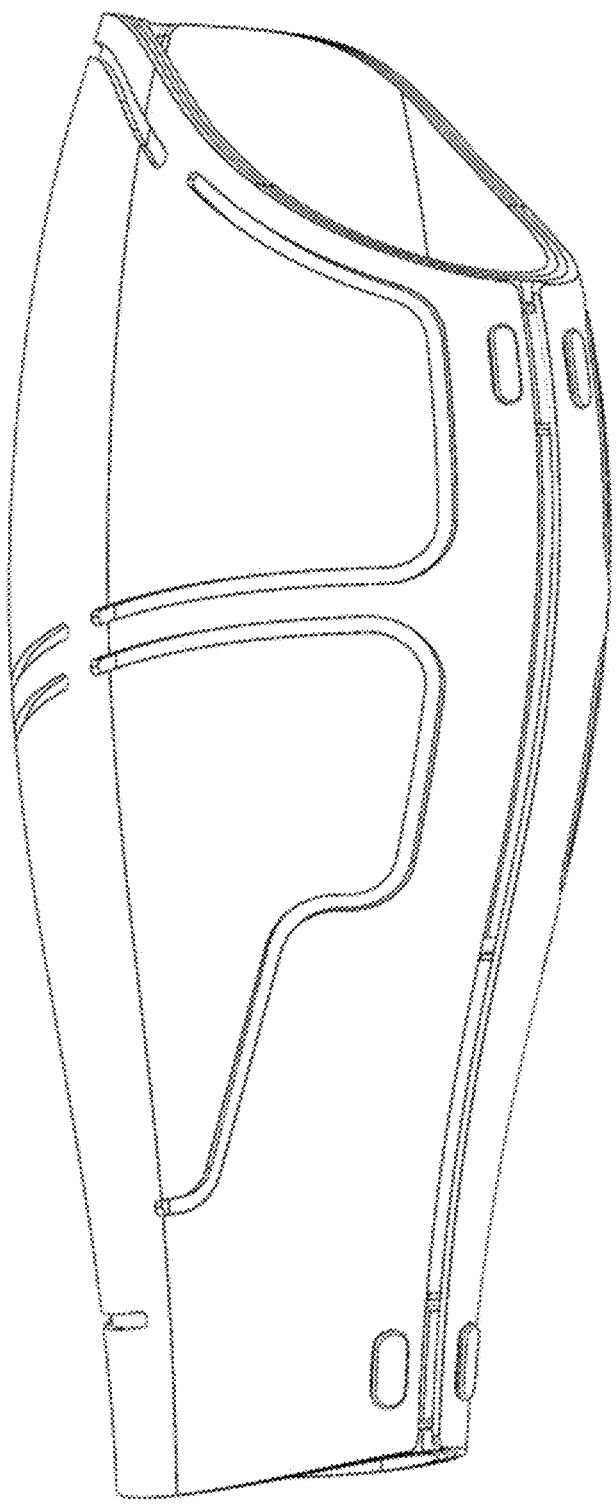
FIG. 7 depicts the cover of FIG. 6 in an assembled configuration without an outer surface.

FIG. 7 depicts a cover 106 of FIG. 6 in an assembled configuration without the outer surface (not shown). The four tabs 161 of the inner layer 160 attach the outer layer 162 and the inner layer 160. The outer layer 162 conceals the controller housing 168.

Figure 8:
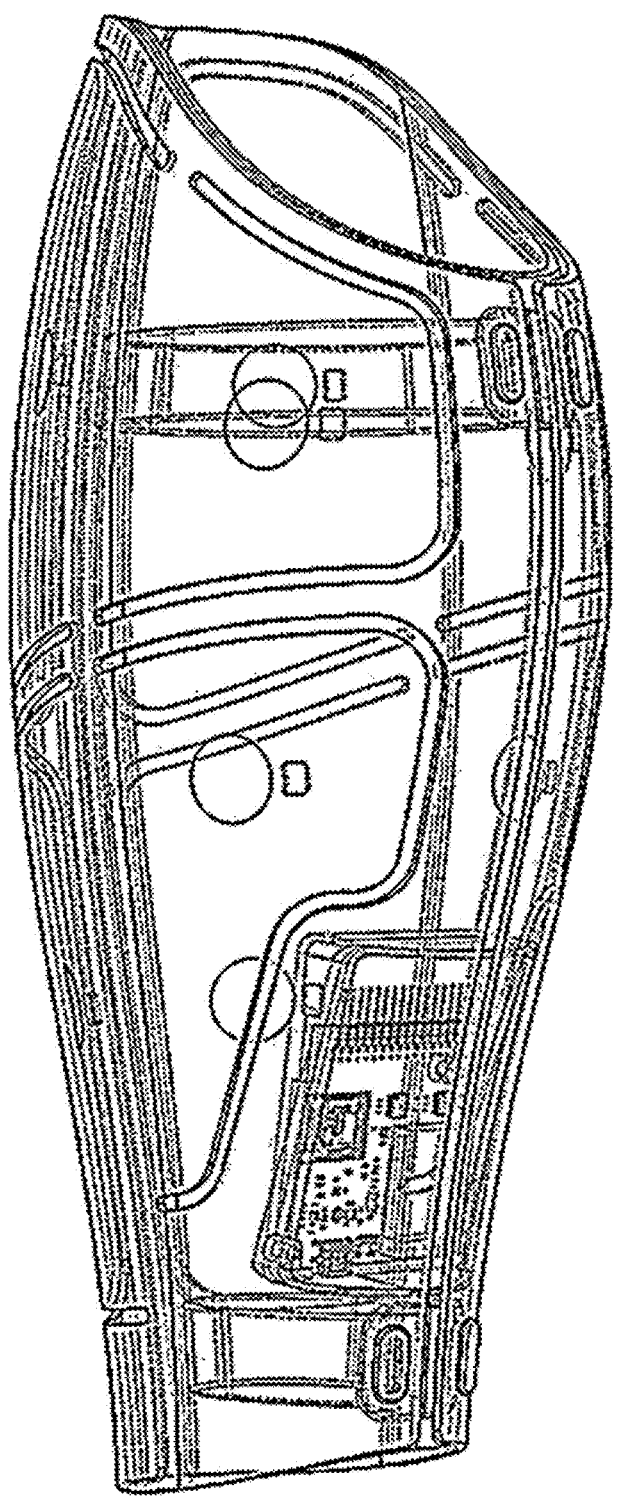
FIG. 8 depicts the cover of FIGS. 6 & 7 in an assembled configuration without the outer surface, in which an outer layer is semi-transparent and a spacer is transparent to show underlying sensors and a sensor controller.

FIG. 8 depicts the cover 106 of FIGS. 6 & 7 in an assembled configuration without the outer surface (not shown), wherein the outer layer 162 is semi-transparent and the spacer 165 is transparent to show the underlying sensors 107 and printed circuit board assembly 167.

Figure 9:
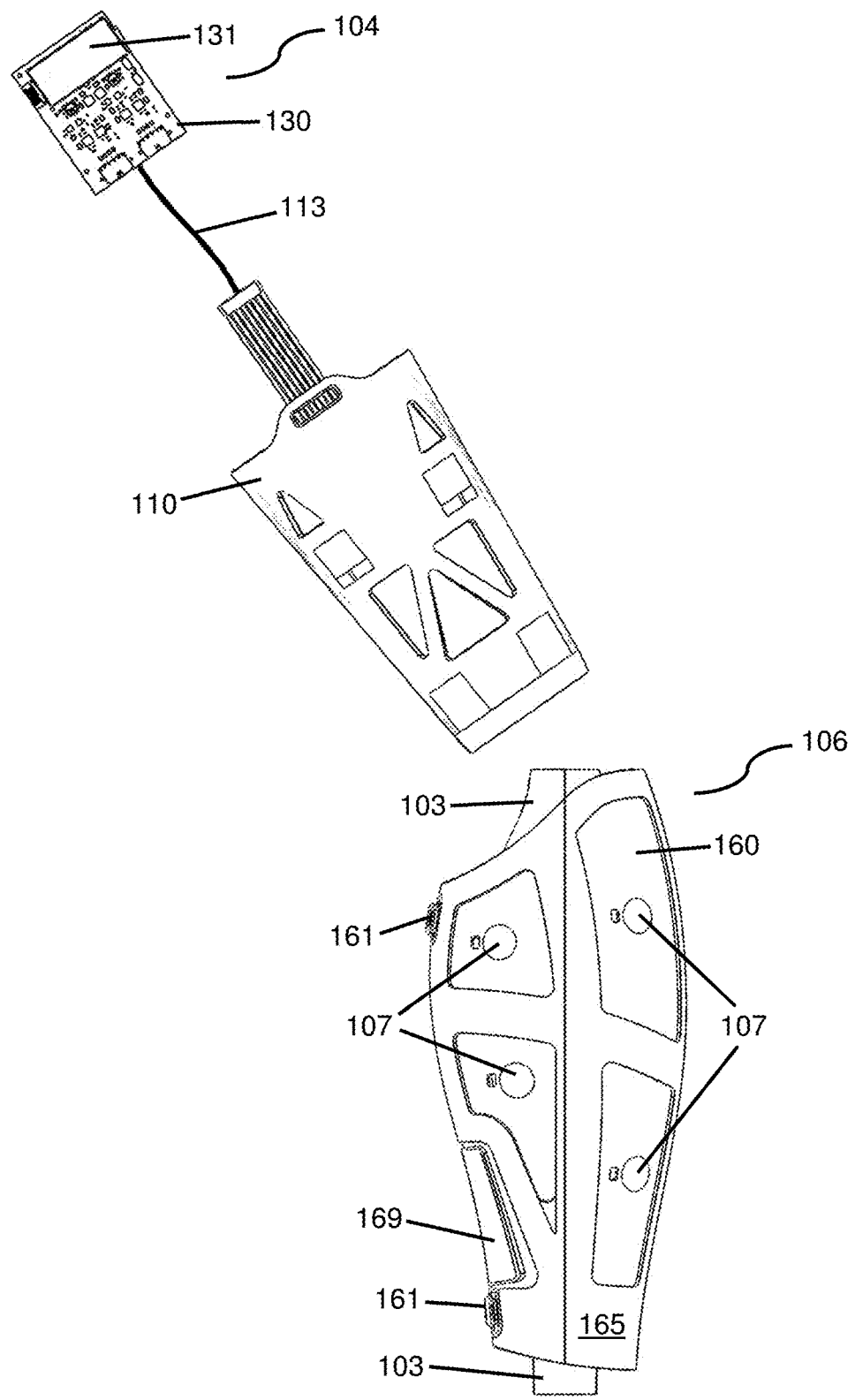
FIG. 9 depicts the substrate and electrode controller of FIG. 3 and a partially-assembled cover according to FIG. 6-8.

FIG. 9 depicts the electrode controller 104 and liner 110 of FIG. 3 and a partially-assembled cover 106 of FIG. 6-8.

Various aspects of this disclosure relate to a method of using a system described anywhere in this disclosure.

In some embodiments, the method is a method to modulate nerve activation in a residual limb of an amputee.

Each amputee has a missing body part. In some embodiments, the amputee presents with phantom limb syndrome.

In some embodiments, the system comprises a cover, and the method comprises attaching the cover to a prosthesis. In some specific embodiments, the method comprises inserting a foam between the cover and the prosthesis to attach the cover to the prosthesis. In some very specific embodiments, the method comprises inserting an expandable foam between the cover and the prosthesis to attach the cover to the prosthesis.

In some embodiments, the system comprises a liner, and the method comprises attaching the liner to the residual limb. In some specific embodiments, the liner comprises an array of electrodes, and the method comprises attaching the liner to the residual limb such that each electrode of the array of electrodes is in electrical communication with the residual limb. In some very specific embodiments, attaching the liner to the residual limb comprises attaching each electrode of the array of electrodes to the residual limb such that each electrode is in electrical communication with the residual limb.

In some embodiments, the method comprises contacting the residual limb with a conductive gel to facilitate electrical communication between each electrode of the array of electrodes and the residual limb.

In some embodiments, the method comprises attaching the prosthesis to the residual limb. In some specific embodiments, the method comprises attaching the prosthesis to the residual limb subsequent to attaching the cover to the prosthesis. In some specific embodiments, the method comprises attaching the prosthesis to the residual limb such that the prosthesis fits over a liner. In some very specific embodiments, the method comprises attaching the prosthesis to the residual limb subsequent to attaching the cover to the prosthesis and subsequent to attaching the liner to the residual limb such that the prosthesis fits over the liner.

In some embodiments, the system comprises an array of sensors, and the method comprises contacting one or more of the sensors. In some specific embodiments, the cover comprises an array of sensors, and the method comprises contacting one or more sensors. In some very specific embodiments, contacting the one or more sensors comprises applying at least one modality (e.g., one or both of force and pressure) to the one or more sensors.

In some embodiments, the method comprises contacting one or more of the sensors after attaching the cover to the prosthesis. In some embodiments, the method comprises contacting one or more sensors after attaching the prosthesis to the residual limb. In some specific embodiments, the method comprises contacting one or more sensors after both attaching the cover to the prosthesis and attaching the prosthesis to the residual limb. In some very specific embodiments, the method comprises contacting one or more sensors after attaching the liner to the residual limb, attaching the cover to the prosthesis, and attaching the prosthesis to the residual limb.

In some embodiments, the method comprises detaching the prosthesis from the residual limb and contacting the one or more sensors after detaching the prosthesis from the residual limb. Methods of this disclosure advantageously allow an amputee to transmit electrical current through his or her residual limb, optionally to treat symptoms of phantom limb syndrome, when the amputee is not wearing a prosthesis with the cover, for example, after the amputee has removed such a prosthesis to sleep.

In some embodiments, contacting the one or more sensors causes an electrode of the array of electrodes to transmit electrical current to the residual limb and another electrode of the array of electrodes to receive the electrical current from the residual limb.

In some embodiments, contacting the one or more sensors after attaching the cover to the prosthesis causes an electrode of the array of electrodes to transmit electrical current to the residual limb and another electrode of the array of electrodes to receive the electrical current from the residual limb. In some embodiments, contacting the one or more sensors after attaching the prosthesis to the residual limb causes an electrode to transmit electrical current to the residual limb and another electrode to receive the electrical current from the residual limb. In some specific embodiments, contacting the one or more sensors after both attaching the cover to the prosthesis and attaching the prosthesis to the residual limb causes an electrode to transmit electrical current to the residual limb and another electrode to receive the electrical current from the residual limb. In some very specific embodiments, contacting the one or more sensors after attaching the liner to the residual limb, attaching the cover to the prosthesis, and attaching the prosthesis to the residual limb causes an electrode to transmit electrical current to the residual limb and another electrode to receive the electrical current from the residual limb.

In some embodiments, contacting the one or more sensors after detaching the prosthesis from the residual limb causes an electrode to transmit electrical current to the residual limb and another electrode to receive the electrical current from the residual limb.

In some embodiments, the method comprises stimulating $A\beta$ nerve fibers in the residual limb. In some specific embodiments, the method comprises stimulating myelinated $A\beta$ nerve fibers in the residual limb, wherein transmitting electrical current to the residual limb stimulates the myelinated $A\beta$ nerve fibers in the residual limb.

In some embodiments, the method comprises modulating the activation of $A\delta$ nerve fibers in the residual limb. In some specific embodiments, the method comprises modulating the activation of myelinated $A\delta$ nerve fibers in the residual limb, wherein transmitting electrical current to the residual limb modulates the activation of the myelinated $A\delta$ nerve fibers in the residual limb.

In some embodiments, the method comprises modulating the activation of C nerve fibers in the residual limb. In some specific embodiments, the method comprises modulating the activation of unmyelinated C nerve fibers in the residual limb, wherein transmitting electrical current to the residual limb modulates the activation of the unmyelinated C nerve fibers in the residual limb.

In some embodiments, the system is configured such that the electrical current treats one or more symptoms of the phantom limb syndrome. In some specific embodiments, the system is configured such that the electrical current treats one or more symptoms of the phantom limb syndrome, and contacting the one or more sensors treats the one or more symptoms by causing the transmitting of electrical current through the residual limb.

In some embodiments, the method comprises detaching the prosthesis from the residual limb and contacting the one or more sensors after detaching the prosthesis from the residual limb; and contacting the one or more sensors after detaching the prosthesis from the residual limb treats the one or more symptoms by causing the transmitting of electrical current through the residual limb.

In some embodiments, the method comprises directing the secondary controller to cause an electrode to transmit electrical current to the residual limb and another electrode to receive the electrical current from the residual limb. In some specific embodiments, the method comprises directing the secondary controller to cause an electrode to transmit electrical current to the residual limb and another electrode to receive the electrical current from the residual limb without contacting the one or more sensors (i.e., the secondary controller bypasses the array of sensors).

Directing the secondary controller may comprise, for example, pressing an icon on a touchscreen graphical user interface of the secondary controller.

In some embodiments, directing the secondary controller to cause the electrode to transmit electrical current to the residual limb and another electrode to receive the electrical current from the residual limb treats the one or more symptoms by transmitting electrical current through the residual limb.

In some embodiments, the method comprises directing a secondary controller in wireless communication with the system to cause one or more positive electrodes of the array of electrodes to transmit electrical current to the residual limb and one or more negative electrodes of the array of electrodes to receive the electrical current from the residual limb. In some specific embodiments, directing the secondary controller to cause the one or more positive electrodes to transmit the electrical current and the one or more negative electrodes to receive the electrical current treats one or more symptoms of the phantom limb syndrome by transmitting the electrical current through the residual limb.

In some embodiments, the method comprises either (1) contacting one or more sensors to cause the one or more positive electrodes to transmit electrical current to the residual limb and the one or more negative electrodes to receive the electrical current from the residual limb in response to a symptom of the phantom limb syndrome or (2) directing the secondary controller to cause the one or more positive electrodes to transmit electrical current to the residual limb and the one or more negative electrodes to receive the electrical current from the residual limb in response to the symptom, and the method treats the phantom limb syndrome by transmitting the electrical current through the residual limb in response to the symptom.

In some embodiments, the method comprises transmitting electrical current through the residual limb from a positive electrode of the array of electrodes to a negative electrode of the array of electrodes periodically over a period of time such as a course of at least 28 days. In some specific embodiments, the method comprises transmitting electrical current through the residual limb from the positive electrode to the negative electrode periodically over the period of time, and the method is effective at reducing symptoms of the phantom limb syndrome as assessed with a Visual Analog Scale following the period of time.

In some embodiments, periodically means at least three times per week, at least four times per week, at least five times per week, at least six times per week, at least seven times per week, at least daily, or at least twice per day.

In some embodiments, periodically means three times per week, four times per week, five times per week, six times per week, seven times per week, daily, or twice per day.

In some embodiments, the period of time is at least one hour, at least 24 hours, at least 48 hours, at least one week, at least 28 days, at least one month, at least six months, or at least one year.

In some embodiments, the period of time is one hour, 24 hours, 48 hours, one week, 28 days, one month, six months, or one year.

In some embodiments, the method comprises contacting the one or more sensors of the array of sensors and transmitting electrical current through the residual limb from a positive electrode of the array of electrodes to a negative electrode of the array of electrodes periodically over a period of time such as a course of at least 28 days. In some specific embodiments, the method comprises contacting the one or more sensors and transmitting electrical current through the residual limb from the positive electrode to the negative electrode periodically over the period of time, and the method is effective at reducing symptoms of the phantom limb syndrome as assessed with a Visual Analog Scale following the period of time.

In some embodiments, the phantom limb syndrome has a first symptom and a second symptom.

In some embodiments, transmitting electrical current through the residual limb from a first positive electrode of the array of electrode to a first negative electrode of the array of electrodes is more effective at treating the first symptom than transmitting and receiving electrical current from other electrodes of the array of electrodes; and the method comprises transmitting electrical current through the residual limb from the first positive electrode to the first negative electrode in response to the first symptom.

In some embodiments, the first positive electrode has a first positive electrode relative position; the first negative electrode has a first negative electrode relative position; and the amputee associates the first symptom with one or both of the first positive electrode relative position and the first negative electrode relative position.

In some embodiments, transmitting electrical current through the residual limb from a second positive electrode of the array of electrode to a second negative electrode of the array of electrodes is more effective at treating the second symptom than transmitting and receiving electrical current from other electrodes of the array of electrodes, and the method comprises transmitting electrical current through the residual limb from the second positive electrode to the second negative electrode in response to the second symptom.

In some embodiments, the second positive electrode has a second positive electrode relative position; the second negative electrode has a second negative electrode relative position; and the amputee associates the second symptom with one or both of the second positive electrode relative position and the second negative electrode relative position.

In some embodiments, the method comprises contacting a first sensor of the array of sensors that corresponds to the first positive electrode and the first negative electrode in response to the first symptom.

In some embodiments, the first sensor has a first sensor relative position, and the amputee associates the first symptom with the first sensor relative position. In some specific embodiments, the first sensor has a first sensor relative position; the first positive electrode has a first positive electrode relative position; the first negative electrode has a first negative electrode relative position; and the amputee associates the first symptom with one, two, or each of the first sensor relative position, the first positive electrode relative position, and the first negative electrode relative position.

In some embodiments, the method comprises contacting a second sensor of the array of sensors that corresponds to the second positive electrode and the second negative electrode in response to the second symptom.

In some embodiments, the second sensor has a second sensor relative position, and the amputee associates the second symptom with the second sensor relative position. In some specific embodiments, the second sensor has a second sensor relative position; the second positive electrode has a second positive electrode relative position; the second negative electrode has a second negative electrode relative position; and the amputee associates the second symptom with one, two, or each of the second sensor relative position, the second positive electrode relative position, and the second negative electrode relative position.

In some embodiments, the method comprises directing the electrode controller (optionally by a secondary controller) to direct the first positive electrode to transmit electrical current to the residual limb and the first negative electrode to receive the electrical current in response to the first symptom.

In some embodiments, the method comprises directing the electrode controller (optionally by a secondary controller) to direct the second positive electrode to transmit electrical current to the residual limb and the second negative electrode to receive the electrical current in response to the second symptom.

In some embodiments, the method comprises contacting a first sensor in response to the first symptom and contacting a second sensor in response to the second symptom over a period of time such as a course of at least 28 days, wherein the method is effective at reducing chronic symptoms of the phantom limb syndrome independent from treating acute symptoms by generating electrical current in the residual limb over the period of time. In some specific embodiments, reduction in chronic symptoms of the phantom limb syndrome is assessed with a Visual Analog Scale. Without limiting this specification or any patent claim that matures from this disclosure, repeated use of the systems of this disclosure reduces chronic symptoms of phantom limb syndrome, which can optionally be assessed with a Visual Analog Scale.

Treating an acute symptom refers to treating a symptom while a subject experiences the symptom, and acute efficacy refers to real-time efficacy at alleviating the acute symptom. Reducing chronic symptoms refers to reducing one or both of the frequency and severity of the symptom over time. Reducing chronic symptoms of the phantom limb syndrome independent from treating acute symptoms refers to reducing one or both of the frequency and severity of the symptom over time independent from treating an acute symptom; for example, after using a system described herein for a period of time (such as a course of at least 28 days), a subject may find that he or she experiences less frequent symptoms of phantom limb syndrome and that the symptoms are less severe independent from whether the subject actually treats any given symptom with the system.

Each amputee has a brain that comprises a somatosensory cortex. In some embodiments, the method is effective to activate different areas of the somatosensory cortex when different electrodes of the array of electrodes transmit and receive electrical current to and from the residual limb.

Without limiting this specification or any patent claim that matures from this disclosure, repeated use of the systems of this disclosure reduces chronic symptoms of phantom limb syndrome by neuromodulation in the somatosensory cortex.

The somatosensory cortex of the brain of an amputee typically includes a region for processing sensations of the missing body part. In some embodiments, the method comprises transmitting electrical current through the residual limb from electrodes of the array of electrodes periodically over a period of time such as a course of at least 28 days; and the method is effective to cause neuromodulation such that the electrical current causes activation in the region for processing sensations of the missing body part following the period of time. In some specific embodiments, the method comprises contacting one or more sensors and transmitting electrical current through the residual limb from a corresponding two or more electrodes periodically over the period of time; and the method is effective to cause neuromodulation such that the electrical current causes activation in the region for processing sensations of the missing body part following the period of time. In some very specific embodiments, the method comprises contacting the one or more sensors in response to a symptom of the phantom limb syndrome.

In some embodiments, the method comprises contacting two or more sensors to transmit electrical current through the residual limb from two or more different positive electrodes to two or more different negative electrodes periodically over a period of time such as a course of at least 28 days; and the method is effective to cause neuroplasticity-driven cortical remapping in the somatosensory cortex of the brain of the amputee following the period of time such that electrical current transmitted through the residual limb activates different areas of the somatosensory cortex after the period of time relative to before the period of time.

Figure 10:
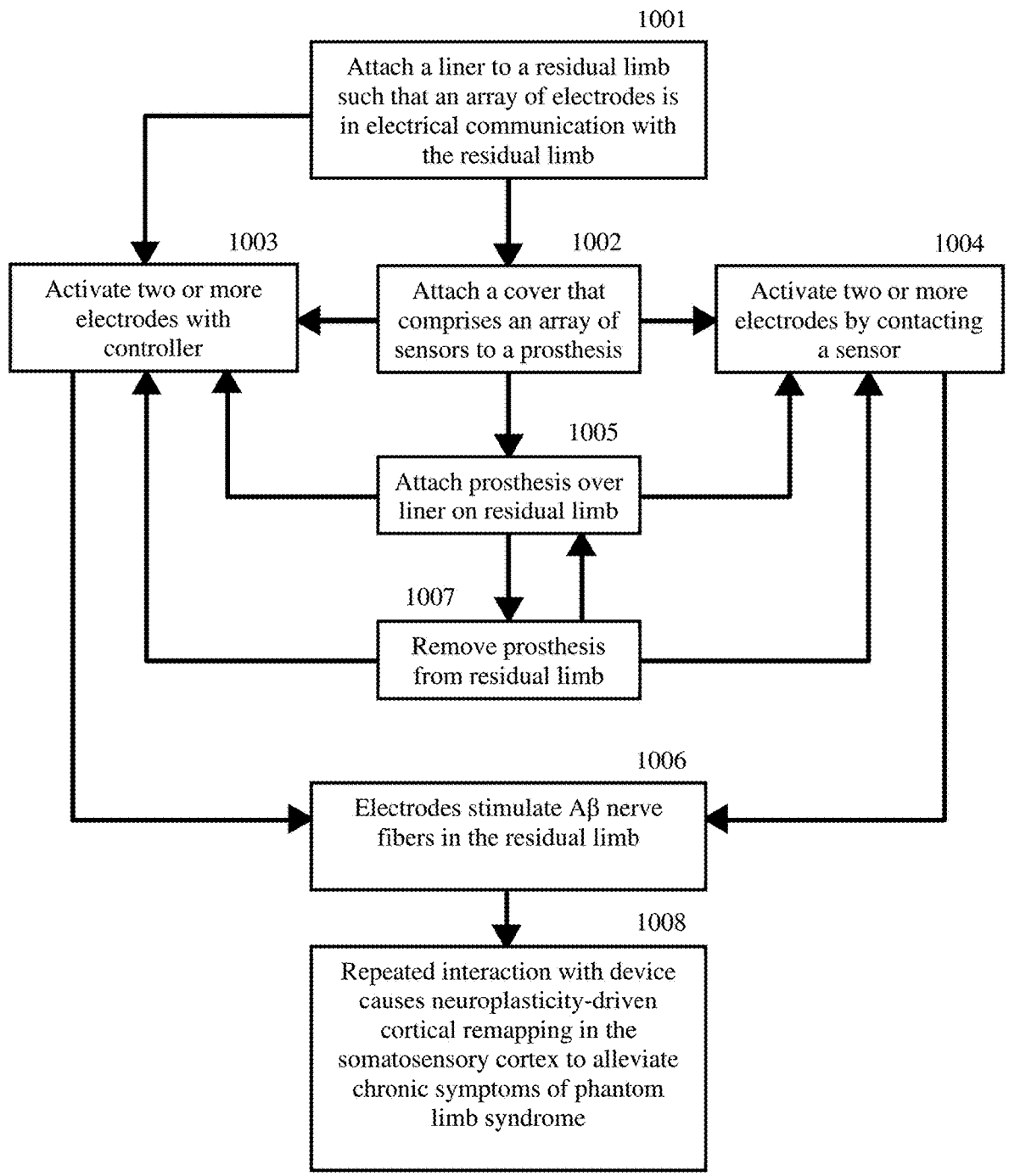
FIG. 10 is a flowchart that depicts use of the system.

FIG. 10 depicts a method of using a system as described herein. An amputee may either first attach a liner to his or her residual limb such that each electrode of the array of electrodes is in electrical communication with the residual limb 1001 or attach a cover to his or her prosthesis 1002. After the amputee attaches the liner to his or her residual limb 1001, the amputee can direct a controller to cause an electrode to transmit electrical current to the residual limb and another electrode to receive the electrical current from the residual limb 1003. The controller may be either an electrode controller or a secondary controller as described herein. After the cover is attached to the prosthesis 1002, contacting one or more sensors of an array of sensors of the cover will cause an electrode to transmit electrical current to the residual limb and another electrode to receive the electrical current from the residual limb 1004. Transmitting electrical current to the residual limb stimulates the Aβ nerve fibers in the residual limb 1006, which can treat one or more symptoms of phantom limb syndrome as described herein. The amputee can advantageously detach the prosthesis from the residual limb 1007 and nevertheless still direct the controller to transmit electrical current to the residual limb 1003 and also contact one or more sensors to transmit electrical current to the residual limb 1004, for example, to treat symptoms of phantom limb syndrome when the amputee is not wearing the prosthesis such as after the amputee has removed the prosthesis to sleep. Repeated use of the system over a period of time is generally effective at reducing chronic symptoms of phantom limb syndrome 1008, for example, as assessed with a Visual Analog Scale, independent from treating acute symptoms by generating electrical current in the residual limb. Without limiting this specification or any patent claim that matures from this disclosure, reduction in chronic symptoms of phantom limb syndrome 1008 are caused by neuroplasticity-driven cortical remapping in the somatosensory cortex of the brain, which can be assessed by scalp electroencephalography ("EEG").

In some embodiments, the method comprises simultaneously performing scalp EEG on the amputee and transmitting electrical current through the residual limb from a first positive electrode to a first negative electrode during the EEG to produce an electrogram.

In some embodiments, the method comprises simultaneously performing EEG on the amputee and transmitting electrical current through the residual limb from a positive electrode of the array of electrodes to a negative electrode of the array of electrodes during the EEG to produce an electrogram that depicts activation of the somatosensory cortex in response to the electrical current; and the system is configured such that the region for processing sensations of the missing body part displays activation in response to the electrical current in the electrogram. In some specific embodiments, simultaneously performing EEG on the amputee and transmitting the electrical current through the residual limb is performed a period of time, such as a course of at least 28 days, after an amputee first began using the system. In some very specific embodiments, the method comprises contacting one or more sensors of the array of sensors to transmit electrical current through the residual limb over a period of time such as a course of at least 28 days, wherein the EEG is performed following the period of time.

In some embodiments, the method comprises simultaneously performing EEG on the amputee and transmitting electrical current through the residual limb from a first positive electrode to a first negative electrode during the EEG to produce an electrogram that depicts activation of the somatosensory cortex in response to the electrical current; the method comprises simultaneously performing EEG on the amputee and transmitting electrical current through the residual limb during the EEG from a second positive electrode to a second negative electrode to produce an electrogram that depicts activation of the somatosensory cortex in response to the electrical current; and the system is configured such that the first positive electrode and the first negative electrode activate a first position in the somatosensory cortex, the second positive electrode and the second negative electrode activate a second position in the somatosensory cortex, and the electrogram depicts that electrical current transmitted through the residual limb by the first positive electrode to the first negative electrode activates different areas of the somatosensory cortex than electrical current transmitted through the residual limb by the second positive electrode to the second negative electrode. In some specific embodiments, the method comprises contacting a first sensor, which corresponds to the first positive electrode and the first negative electrode, to transmit electrical current through the residual limb periodically over a period of time such as a course of at least 28 days; and the method comprises contacting a second sensor, which corresponds to the second positive electrode and the second negative electrode, to transmit electrical current through the residual limb periodically over the period of time, wherein the EEG is performed following the period of time. Without limiting this specification or any patent claim that matures from this disclosure, neuromodulation in the somatosensory cortex by the systems of this disclosure may be detected with an EEG.

The following Exemplification describes a contemplated pilot clinical trial to illustrate certain aspects of this disclosure, and the Exemplification shall not be construed to limit this disclosure or any patent claim that matures from this disclosure.

Exemplification

A pilot clinical trial demonstrates that transcutaneous electrical stimulation of a residual limb in response to touching a prosthesis reduces symptoms of phantom limb syndrome.

A group of 15 amputee subjects who experience symptoms of phantom limb syndrome as a result of limb amputation are enrolled in a pilot clinical trial. Each subject has an intact limb that corresponds to the amputated limb. The subjects rate their level of pain associated with phantom limb syndrome using a Visual Analog Scale.

A system as described in the detailed description is provided to each subject. Briefly, the system comprises a prosthetic cover comprising an array of sensors, which control the activation of an array of electrodes in a liner that fits over the residual limb of an amputee.

Each subject is fitted with a liner, such that each electrode of the array of electrodes is in electrical communication with the residual limb. Each subject has an existing prosthetic, which is fitted with a cover comprising an array of sensors.

Each subject is fitted with EEG electrodes. Various regions of the intact limb are contacted by a researcher, and an electrogram is recorded for the intact limb. Then, while each subject is wearing his or her existing prosthetic, various regions of the cover of the prosthetic are contacted by the researcher to drive electrical current through the residual limb, and an electrogram is recorded for the prosthetic cover. The subject is instructed to watch as the intact limb and cover are contacted. The various regions of the intact limb and cover that are contacted correspond to each other both spatially and temporally.

Each subject is then instructed to apply pressure to his or her intact limb in a similar spatial and temporal pattern as the researcher while focusing his or her gaze on the areas of applied pressure, and an electrogram is recorded. Each subject is then instructed to apply pressure to his or her prosthetic cover in a similar spatial and temporal pattern as the researcher while focusing his or her gaze on the areas of applied pressure, and an electrogram is recorded.

Each subject is then instructed to take the system home. Each subject is given written instructions to apply pressure to the intact limb and prosthetic cover daily in the spatial and temporal pattern and to otherwise apply pressure to the prosthetic cover in response to symptoms of phantom limb syndrome as well as upon demand. Use of the system is recorded by the system in its computer memory. Each subject is also instructed to rate his or her level of pain associated with phantom limb syndrome on the Visual Analog Scale daily both before and after performing the written instructions.

After four weeks, each subject returns for a follow-up EEG, which is performed with substantially the same spatial and temporal contact pattern for the intact limb and prosthetic cover as administered for the initial EEG described above. The initial and follow-up electrograms are approximately the same for each intact limb. The initial and follow-up electrograms are significantly different for each amputated limb. For subjects with leg amputations, differences are greater for gamma waves detected near the medial region of the somatosensory cortex. The magnitude of difference between initial and follow-up EEGs correlates with frequency of system use as recorded by the system.

These results indicate that the intervention results in neuroplasticity-driven cortical remapping in the subjects.

Following four weeks of the intervention, all subjects report lower levels of phantom limb pain on the Visual Analog Scale relative to before the intervention, which indicates long-term efficacy of the intervention. The magnitude in reduction of pain as reported on the Visual Analog Scale correlates with frequency of system use as recorded by the system. Following four weeks of the intervention, all subjects report lower levels of phantom limb pain on the Visual Analog Scale following performance of the spatial and temporal pattern intervention relative to immediately prior to the intervention, which indicates acute efficacy of the intervention.

What is claimed is:

1. A system for modulating nerve activation in a residual limb of an amputee, comprising:
a cover configured to overlay an outer surface of an arm portion of an upper extremity prosthesis, a leg portion of an above knee prosthesis or a leg portion of a below knee prosthesis, the cover comprising:
an outer layer, the outer layer including:
a plurality of actuators configured to depress responsive to a force or pressure applied by a user; and
an inner layer including:
a plurality of sensors configured to sense the force or the pressure applied to the at least one of the plurality of actuators; and
a liner including a plurality of electrodes in communication with the plurality of sensors and configured to receive the residual limb,
wherein the plurality of electrodes are activated in response to one or more of the sensors sensing the force or the pressure, and transmit electrical current to stimulate nerve fibers in the residual limb when the electrode is in electrical communication with the residual limb.

2. The system of claim 1, wherein each sensor corresponds to an electrode.

3. The system of claim 1, wherein the electrical current is pulsed electrical current.

4. The system of claim 1, wherein the plurality of electrodes are arranged in an array.

5. The system of claim 1, wherein transmitting the electrical current to the residual limb reduces one or more symptoms of phantom limb syndrome.

6. A method to modulate nerve activation in a residual limb of an amputee, comprising:
providing a system that comprises a cover and a liner, wherein the cover is configured to overlay an outer surface of an arm portion of an upper extremity prosthesis, a leg portion of an above knee prosthesis or a leg portion of a below knee prosthesis, the cover comprising:
an outer layer, the outer layer including:
a plurality of actuators configured to depress responsive to a force or pressure applied by a user; and
an inner layer including:
a plurality of sensors configured to sense the force or the pressure from at least one of the plurality of actuators, and
wherein the liner includes a plurality of electrodes in communication with the plurality of sensors and the liner is configured to receive the residual limb;
attaching the cover to the arm portion of an upper extremity prosthesis, the leg portion of an above knee prosthesis or the leg portion of a below knee prosthesis;
attaching the liner to the residual limb such that each electrode of the plurality of electrodes is in electrical communication with the residual limb;
attaching the prosthesis to the residual limb;
depressing one or more of the actuators with the force or the pressure;
sensing, with each sensor, the force or the pressure on the one or more actuators; and
stimulating nerve fibers in the residual limb.

7. The method of claim 6, wherein each sensor corresponds to an electrode.

8. The method of claim 6, further comprising:
transmitting electrical current to the residual limb, with an electrode, responsive to the sensor sensing the force or the pressure.

9. The method of claim 8, further comprising:
stimulating the nerve fibers in the residual limb responsive to transmitting the electrical current.

10. The method of claim 6, wherein:
the system comprises an electrode controller in electrical communication with each electrode of the plurality of electrodes; and
further comprising:
transmitting, with the electrode controller, the electrical current, via the electrodes, to the residual limb.

11. A method to treat phantom limb syndrome in an amputee, comprising:
providing a system that comprises a cover and a liner, wherein the cover is configured to overlay an outer surface of an arm portion of an upper extremity prosthesis, a leg portion of an above knee prosthesis or a leg portion of a below knee prosthesis, the cover comprising:
an outer layer, the outer layer including:
a plurality of actuators configured to depress responsive to a force or pressure applied by a user; and
an inner layer including:
a plurality of sensors configured to sense the force or the pressure from at least one of the plurality of actuators, and
wherein the liner includes a plurality of electrodes in communication with the plurality of sensors and the liner is configured to receive the residual limb;
attaching the cover to the arm portion of an upper extremity prosthesis, the leg portion of an above knee prosthesis or the leg portion of a below knee prosthesis;
attaching the liner to a residual limb such that each electrode of the plurality of electrodes is in electrical communication with the residual limb;
attaching the prosthesis to the residual limb;
depressing one or more of the actuators with the force or the pressure;
sensing, with each sensor, the force or the pressure on the one or more actuators; and
stimulating nerve fibers in the residual limb.

12. The method of claim 11, wherein each sensor corresponds to at least two electrodes, and each electrode corresponds to at least one sensor.

13. The method of claim 11, further comprising:
transmitting electrical current to the residual limb, with at least one of the plurality of electrodes, responsive to the sensor sensing the force or the pressure.

14. The method of claim 13, further comprising:
stimulating the nerve fibers in the residual limb responsive to transmitting the electrical current; and
evoking a somatic sensation that a missing limb is intact responsive to stimulating the nerve fibers.

15. The system of claim 1, further comprising:
a controller, wherein the controller is in communication with the plurality of electrodes and transmits electrical current to the residual limb, via the electrodes, when the electrodes are in electrical communication with the residual limb.

16. The system of claim 15, wherein:
the controller is a mobile computing device; and
wireless communication is mediated by one or both of a Bluetooth or Wi-Fi connection between the mobile computing device and the plurality of electrodes.

17. The system of claim 1, further comprising:
a spacer located between the inner layer and the outer layer.

18. The system of claim 1, wherein each actuator is configured as a flex panel.

19. The system of claim 18, wherein each flex panel has a surface area larger than a surface area of each of the plurality of the sensors such that depressing any portion of an actuator transduces a force or pressure to at least one of the sensors.

20. The method of claim 6, further comprising:
selectively pressing the actuators to apply the force or the pressure at a desired location.

21. The system of claim 1, wherein the plurality of sensors has a three-dimensional configuration in the shape of a leg or arm.

22. The method of claim 10, further comprising:
bypassing the sensors, with the controller, to cause each electrode to transmit electrical current to the residual limb.

23. The method of claim 10, further comprising:
transmitting, with the controller, electrical current through the residual limb when the amputee is not wearing the cover.

24. The method of claim 10, further comprising:
tracking the amputee's use of the system;
developing a pattern that displays a high probability of efficaciously treating phantom limb syndrome; and
running, with the controller, programs to implement the pattern.

25. The method of claim 24, further comprising:
wherein the pattern includes data from crowd-sourced use records from a plurality of amputees.

* * * * *